(12) United States Patent
Nakagawa et al.

(10) Patent No.: US 8,843,325 B2
(45) Date of Patent: Sep. 23, 2014

(54) INDIVIDUAL INFORMATION DETERMINING METHOD, INDIVIDUAL INFORMATION DETERMINING DEVICE, ELECTRONIC APPARATUS, AND INDIVIDUAL INFORMATION DETERMINING PROGRAM

(75) Inventors: Kazuhiro Nakagawa, Saitama (JP); Hatsume Uno, Kanagawa (JP); Masahiro Matsumoto, Kanagawa (JP); Tomoko Katsuhara, Kanagawa (JP); Yuuki Watanabe, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 13/430,285

(22) Filed: Mar. 26, 2012

(65) Prior Publication Data

US 2013/0078651 A1    Mar. 28, 2013

(30) Foreign Application Priority Data

Mar. 31, 2011    (JP) ................... 2011-077455
Aug. 3, 2011    (JP) ................... 2011-170171

(51) Int. Cl.
*A61B 5/00*    (2006.01)
*G01N 33/72*    (2006.01)
*G01N 33/94*    (2006.01)
*G01N 33/53*    (2006.01)
*G06F 19/00*    (2011.01)

(52) U.S. Cl.
CPC .............. *G01N 33/53* (2013.01); *G01N 33/721* (2013.01); *G01N 33/9413* (2013.01); *G06F 19/3431* (2013.01)
USPC ................. 702/32; 702/19; 702/22; 600/309; 422/105; 435/3

(58) Field of Classification Search
CPC ......... G06F 19/00; G06F 19/24; G06F 19/30; A61B 5/00; A61B 5/165; A61B 5/167; A61B 5/168; A61B 5/72; A61B 5/68; A61B 5/6801; G01N 33/48
See application file for complete search history.

(56) References Cited

U.S. PATENT DOCUMENTS

| 5,550,050 | A  | * | 8/1996 | Holland et al. ............... 435/382 |
| 2006/0106291 | A1 | * | 5/2006 | Sidelnik et al. ............... 600/300 |
| 2007/0083092 | A1 | * | 4/2007 | Rippo et al. ................... 600/307 |
| 2009/0292183 | A1 | * | 11/2009 | Matsumoto et al. ........... 600/309 |

FOREIGN PATENT DOCUMENTS

| JP | 07-124139 | 5/1995 |
| JP | 2007-016105 | 1/2007 |
| JP | 2007-257002 | 10/2007 |

OTHER PUBLICATIONS

Abercrombie et al., Differential effect of stress on in vivo dopamine release in striatum, nucleus accumbens, and medial frontal cortex, Journal of Neurochemistry-Rapid Communication, vol. 52, No. 5, pp. 1655-1658, 1989.*

Stalenheim et al., Testosterone as a biologcal marker in psychopathy and alcoholism, Psychiatry Research, 77, pp. 79-88, 1998.*

(Continued)

*Primary Examiner* — Melanie Y Brown
*Assistant Examiner* — Rebecca Martinez
(74) *Attorney, Agent, or Firm* — K&L Gates LLP

(57) ABSTRACT

Disclosed in an individual information determining method in which individual information of a subject is determined based on one or a plurality of pieces of biomolecule data collected from a surface of a body surface of the subject.

13 Claims, 25 Drawing Sheets

(56) References Cited

OTHER PUBLICATIONS

Lena et al., Variations in extracellular levels of dopamine, noradrenaline, glutamate, and aspartate across the sleep-wake cycle in the medial prefrontal cortex and nucleus accumbens of freely moving rats, Journal of Neuroscience Research, 81, pp. 891-899, 2005.*

Ray et al., Links between temperamental dimensions and brain monoamines in the rat, Behavioral Neuroscience, vol. 120, No. 1, pp. 85-92, 2006.*

Coates, et al. "Endogenous steroids and financial risk taking on a London trading floor," Proceedings of the National Academy of Sciences, vol. 105, No. 16, Apr. 22, 2008, pp. 6167-6172. (6 pages).

Beaver, K.M., et al., Three dopaminergic polymorphisms are associated with academic achievement in middle and high school, Intelligence (2010), doi:10.1016/j.intell.2010.08.001. (9 pages).

Bodi et al., "Reward-learning and the novelty-seeking personality: a between- and within-subjects study of the effects of dopamine agonists on young Parkinson's patients*," Brain 2009: 132; 2385-2395. (11 pages).

Eisenegger et al., "Prejudice and truth about the effect of testosterone on human bargaining behaviour," NATURE, vol. 463, Jan. 21, 2010, pp. 356-361. (6 pages).

Garcia et al., "Associations between Dopamine D4 Receptor Gene Variation with Both Infidelity and Sexual Promiscuity," PLoS ONE, Nov. 2010, vol. 5, Issue 11, e14162. (6 pages).

Gerra et al., "Homovanillic acid (HVA) plasma levels inversely correlate with attention deficit—hyperactivity and childhood neglect measures in addicted patients," Journal of Neural Transmission, vol. 114, pp. 1637-1647, Epub Aug. 10, 2007.

Giegling et al., "Dopa Decarboxylase and Tyrosine Hydroxylase Gene Variants in Suicidal Behavior," American Journal of Medical Genetics, Part B, Neuropsychiatric Genetics, Apr. 5, 2008, vol. 147B(3), pp. 308-315. (8 pages).

Giegling et al., "Tyrosine Hydroxylase and DOPA Decarboxylase Gene Variants in Personality Traits," Neuropsychobiology, Published online Feb. 17, 2009, vol. 59, pp. 23-27. (6 pages).

van Honk et al. "Testosterone shifts the balance between sensitivity for punishment and reward in healthy young women," Psychoneuroendocrinology, 2004, vol. 29, pp. 937-943. (7 pages).

Oxford et al., "Hormonal responses differ when playing violent video games against an ingroup and outgroup," Evolution and Human Behavior, vol. 31, 2010, pp. 201-209. (9 pages).

Kaasinen et al., "Personality traits and brain dopaminergic function in Parkinson's disease," Proceedings of the National Academy of Sciences, vol. 98, No. 23, Nov. 6, 2001, pp. 13272-13277 (6 pages).

Lynn et al., "Temperament and Character Profiles and the Dopamine D4 Receptor Gene in ADHD," American Journal of Psychiatry, 2005, vol. 162, pp. 906-914. (9 pages).

Levi et al., "Deal or No Deal: Hormones and Completion of Mergers and Acquisitions*," Sauder School of Business, University of British Columbia, Dec. 2008. (36 pages).

Nilsson et al., "Neurochemical measures co-vary with personality traits: Forensic psychiatric findings replicated in a general population sample," Psychiatry Research, vol. 178, May 21, 2010, pp. 525-530. (6 pages).

Nyman et al., "Impact of the Dopamine Receptor Gene Family on Temperament Traits in a Population-Based Birth Cohort," American Journal of Medical Genetics, Part B, Neuropsychiatric Genetics, Sep. 5, 2009, vol. 150B (6), pp. 854-865. (12 pages).

Bos et al., "Testosterone decreases trust in socially naïve humans," Proceedings of the National Academy of Sciences, Early Edition, www.pnas.org/cgi/doi/10.1073/pnas.0911700107. (5 pages).

Reavis et al., "Adult Sex Differences on a Decision-Making Task Previously Shown to Depend on the Orbital Prefrontal Cortex," Behavioral Neuroscience, 2001, vol. 115, No. 1, pp. 196-206. (11 pages).

Ribases et al., "Exploration of 19 serotoninergic candidate genes in adults and children with attention-deficit/hyperactivity disorder identifies association for 5HT2A, DDC and MAOB," Molecular Psychiatry, 2007, accepted Jul. 25, 2007. (15 pages).

Sadahiro et al., "Association study between a functional polymorphism of tyrosine hydroxylase gene promoter and personality traits in healthy subjects," Behavioural Brain Research, vol. 208, No. 1, Mar. 17, 2010, pp. 209-212, Epub Dec. 1, 2009. (4 pages).

Schosser et al., "Interaction between serotonin 5-HT2A receptor gene and dopamine transporter (DAT1) gene polymorphisms influences personality trait of persistence in Austrian Caucasians," The World Journal of Biological Psychiatry, 2010, vol. 11, No. 2, pp. 417-424. (8 pages).

Sheldrick et al., "Effect of COMT val158met genotype on cognition and personality," European Psychiatry, vol. 23, 2008, p. 385-389. (5 pages).

Sher et al., "Lower CSF Homovanillic Acid Levels in Depressed Patients with a History of Alcoholism," Neuropsychopharmacology, 2003, vol. 28, pp. 1712-1719. (8 pages).

Shibuya et al., "The -67 A/T promoter polymorphism in the dopamine transporter gene affects personality traits of Japanese healthy females," Behavioural Brain Research, vol. 203, 2009, pp. 23-26. (4 pages).

Siever et al., "CSF Homovanillic Acid in Schizotypal Personality Disorder," The American Journal of Psychiatry, Jan. 1993, vol. 150, No. 1, ProQuest, pp. 149-151. (3 pages).

Takahashi et al., "Dopamine D1 Receptors and Nonlinear Probability Weighting in Risky Choice," The Journal of Neuroscience, Dec. 8, 2010, vol. 30, No. 49, pp. 16567-16572. (6 pages).

* cited by examiner

FIG. 5

| DOPA | SLEEP | STRESS | PLEASURE | EXERCISE |
|---|---|---|---|---|
| PURSUIT OF NOVELTY | − | − | ↑ | ↓ |
| DAMAGE AVOIDANCE | − | − OR (↑) | − | − |
| COMPENSATION DEPENDENCE | ↓ | − | − | ↑ |
| PERSISTENT TENDENCIES | − | − | ↓ | ↑ |
| SELF-ORIENTATION | − | ↓ | − | − |
| COOPERATIVENESS | − OR (↓) | ↓ | − | ↑ |
| SELF-TRANSCENDENCE | − | − | − | ↓ |

| DA | SLEEP | STRESS | PLEASURE | EXERCISE |
|---|---|---|---|---|
| PURSUIT OF NOVELTY | − | − | − | − |
| DAMAGE AVOIDANCE | − | − | − | ↓ |
| COMPENSATION DEPENDENCE | − | ↓ | − | − |
| PERSISTENT TENDENCIES | ↑ | − | ↓ | − OR (↓) |
| SELF-ORIENTATION | ↓ | ↑ | ↑ | ↑ |
| COOPERATIVENESS | − OR (↓) | − | ↑ | ↑ |
| SELF-TRANSCENDENCE | − | ↓ | − OR (↓) | − |

| DA/DOPA | SLEEP | STRESS | PLEASURE | EXERCISE |
|---|---|---|---|---|
| PURSUIT OF NOVELTY | − | − | − | − OR (↑) |
| DAMAGE AVOIDANCE | − | − OR (↓) | − | ↓ |
| COMPENSATION DEPENDENCE | − | − | − | − |
| PERSISTENT TENDENCIES | − OR (↓) | − | − | ↓ |
| SELF-ORIENTATION | − OR (↓) | ↑ | ↑ | − |
| COOPERATIVENESS | − | − OR (↑) | ↑ | − |
| SELF-TRANSCENDENCE | − | ↓ | − OR (↓) | − |

FIG. 6

TEMPERAMENT: INDIVIDUAL DIFFERENCES IN EMOTIONAL RESPONSE
            TO STIMULI.
            STRONGLY INFLUENCED BY HEREDITY.

· PURSUIT OF NOVELTY:
   PURSUES NEW THINGS, DECISION-MAKING IS FAST, AGGRESSIVE, IMPATIENT,
   AWARENESS OF RULES IS LOW, DYNAMIC

· DAMAGE AVOIDANCE:
   WORRIED, EASILY STRESSED, INTROVERTED, EASILY FATIGUED,
   RISK AVERSE

· COMPENSATION DEPENDENCE:
   SOCIAL, FRIENDLY, DEGREE OF DEPENDENCE ON PEOPLE OR THINGS

· PERSISTENT TENDENCIES:
   PERSEVERANCE

CHARACTER: PERSONALITY WITH RESPECT TO INDIVIDUALLY CHOSEN GOALS
           AND SENSE OF VALUES. DEVELOPED BY LEARNING.

· SELF-ORIENTATION:
   PERCEPTION OF SELF AS AN INDEPENDENT INDIVIDUAL,
   BEHAVIOR ACCORDING TO GOALS AND SENSE OF VALUES

· COOPERATIVENESS:
   CONFIRMATION AND ACCEPTANCE OF OTHER PEOPLE

· SELF-TRANSCENDENCE:
   INSPIRATION, INTUITIVE ABILITY, SENSE OF INTEGRATION WITH
   SURROUNDINGS AND NATURE, DEGREE OF SATISFACTION WITH LIFE

FIG. 8
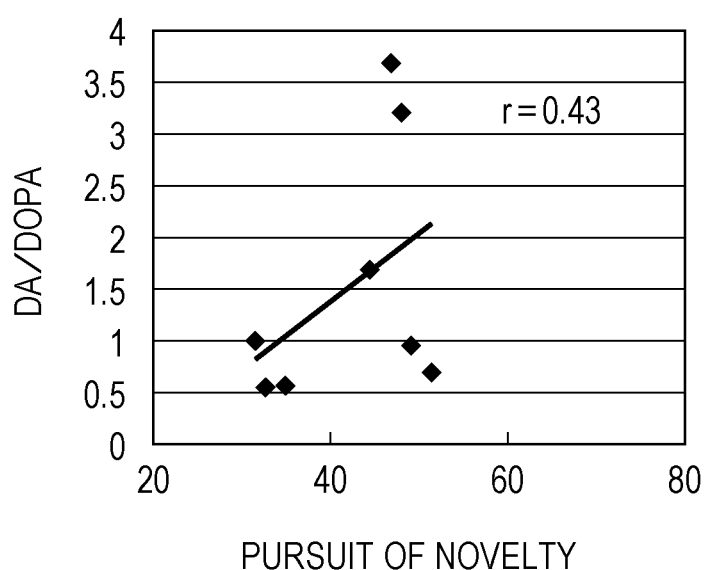
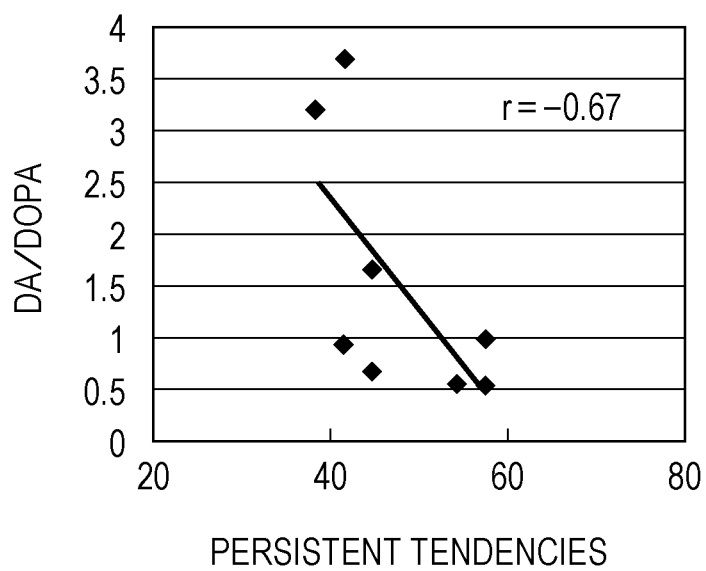

FIG. 15
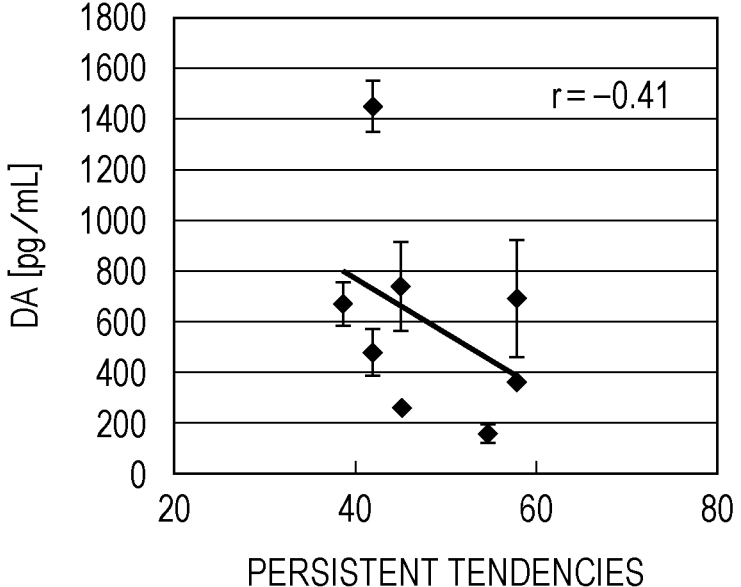
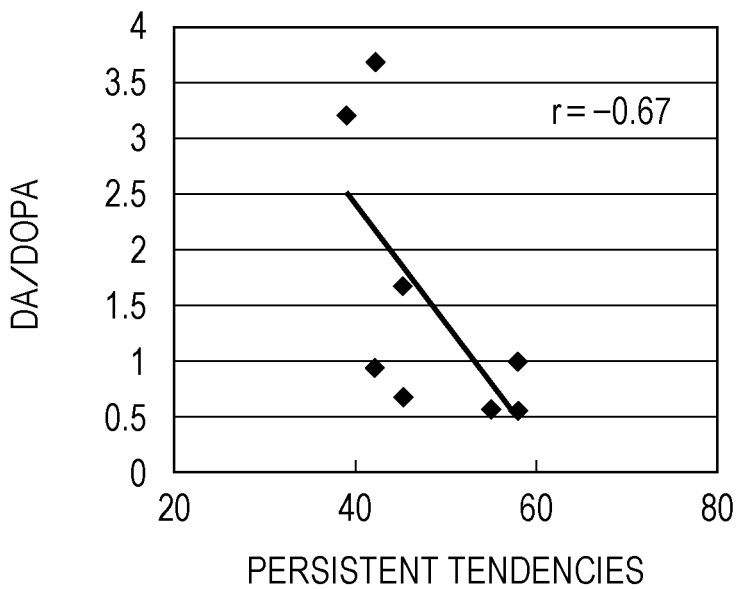

FIG. 21
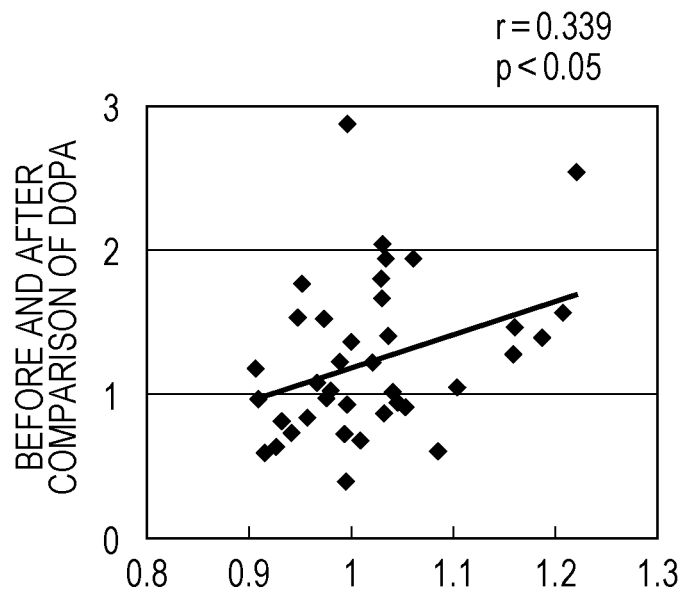
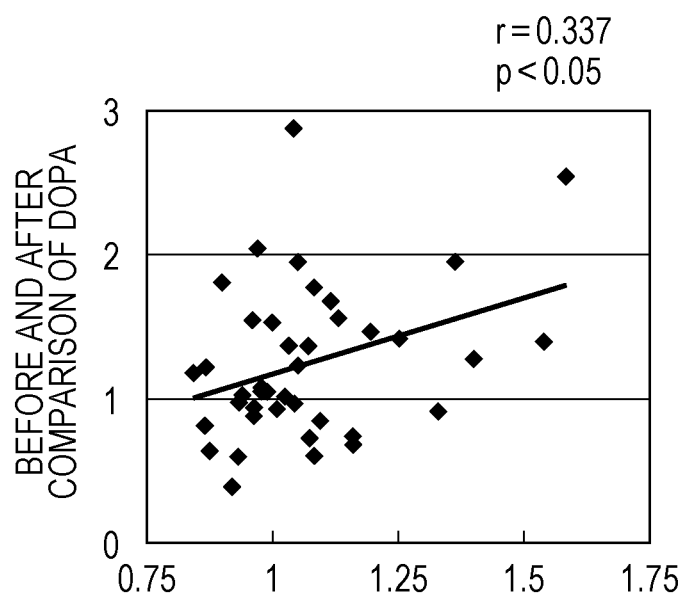

INDIVIDUAL INFORMATION DETERMINING METHOD, INDIVIDUAL INFORMATION DETERMINING DEVICE, ELECTRONIC APPARATUS, AND INDIVIDUAL INFORMATION DETERMINING PROGRAM

CROSS REFERENCES TO RELATED APPLICATIONS

The present application claims priority to Japanese Priority Patent Application JP 2011-077455 filed in the Japan Patent Office on Mar. 31, 2011, and Japanese Priority Patent Application JP 2011-170171 filed in the Japan Patent Office on Aug. 3, 2011, the entire contents of which are hereby incorporated by reference.

BACKGROUND

The present application relates to an individual information determining method, an individual information determining device, an electronic apparatus, and an individual information determining program. More specifically, the present application relates to an individual information determining method based on body surface biomolecule information, an individual information determining device, and an electronic apparatus including this, and an individual information determining program.

The definition and classification of an individual's personality, temperament, and character are effective for activities such as educating and guiding individuals, recommending products, services, behaviors, and the like, measuring the severity and danger of mental disorders, developmental disabilities, and the like, and these are already being put into practical use.

As techniques for defining and classifying an individual's temperament and character, a questionnaire method, a performance testing method, and a method for measuring the response to specific stimuli may be exemplified.

In Japanese Unexamined Patent Application Publication No. 2007-257002, a technique applying the questionnaire method is proposed, in Japanese Unexamined Patent Application Publication No. 2007-16105, a performance testing method is proposed, and, in Japanese Unexamined Patent Application Publication No. 7-124139, stimulus-responses and the like using perspiration in response to images are proposed.

In academic fields such as neuroscience and psychology and in medical fields such as psychiatry, there are several established questionnaire methods, performance testing methods, and projection methods, and, in the field of neuroscience, methods using stimulus-response are widely used.

As the questionnaire method, the five major factors personality test, the Yatabe-Guilford personality test, and the TCI (Temperament and Character Inventory) method are representative examples. Further, as the questionnaire methods used in medical fields, the Hamilton Rating Scale for Depression (HAM-D), the Beck Depression Inventory (BDI), and the like, which are used to evaluate depression symptoms, are representative examples. In addition, a brief psychiatric rating scale (BPRS) and the like used to evaluate schizophrenia and the like are also typical.

As the performance testing method, there are established methods such as the Uchida-Kraepelin psychodiagnostic test involving performing several sets of simple addition, furthermore, many other methods of individual character evaluation have been reported.

The projection method uses the nature of humans to project their own feelings onto other objects and the Rorschach test, which asks what may be seen in an ambiguous image, and suchlike are typical examples thereof.

There are many established methods within these methods; however, since they involve a questionnaire or a performance completed by the subject, the subject is bound to be deprived of their freedom for a certain time. Further, the methods often include stimulation of the feelings in the questioning or the performance itself which a subject may sometimes feel resistance to undergoing.

Incidentally, it is reported that it is often possible to obtain a correlation between polymorphisms in genes relating to the amount of biologically active substances, the production system, and the receptor system and an established character determining method.

Monoamine based molecules acting as neurotransmitters (dopamine, adrenaline, noradrenaline, and serotonin) may be exemplified. For example, it is reported that there is a correlation between the amounts of in vivo monoamine metabolites included in cerebrospinal fluid and in a serum and character determining according to the TCI method (Nilsson, T., S. Psychiatry Res 178(3): 525-30).

In addition, it is widely reported that there is a correlation between polymorphisms in genes relating to the monoamine production system, the receptor system, and the metabolic system, and the tests relating to character determining and feelings according to the TCI method (Giegling, I., D. Moreno-De-Luca, et al. (2008). Am J Med Genet B Neuropsychiatr Genet 147(3): 308-15; Giegling, I., D. Moreno-De-Luca, et al. (2009). Neuropsychobiology 59(1): 23-7; Sadahiro, R., A. Suzuki, et al. Behav Brain Res 208(1): 209-12.2009; Nyman, E. S., A. Loukola, et al. (2009). Am J Med Genet B Neuropsychiatr Genet 150B(6): 854-65. 2009; Schosser, A., K. Fuchs, et al. World J Biol Psychiatry 11(2Pt2): 417-24; Sheldrick, A. J., A. Krug, et al. (2008). Eur Psychiatry 23(6): 385-9; and Shibuya, N., M. Kamata, et al. (2009). Behav Brain Res 203(1): 23-6).

In addition, in patients with Parkinson's disease, it has been reported that there is a tendency for character to change when dopamine agonists are administered (Bodi, N., S. Keri, et al. (2009). Brain 132(Pt9): 2385-95).

There are also more specific reports relating to character, for example, there are reports that there is a correlation between the amount of dopamine receptor and the expected value for risk selection (Takahashi, H., H. Matsui, et al. J Neurosci 30(49): 16567-72). In addition, there are reports that there is a correlation between polymorphisms in genes relating to the dopamine receptor system and the metabolic system and student grades relating to desire (Beaver, K. M., M. G. Vaughn, et al. (2010). Intelligence). In addition, there are reports that there is a correlation between polymorphisms in genes relating to the dopamine receptor system and sexual preference (Garcia, J. R., J. MacKillop, et al. PLoS One 5(11):e14162).

It is understood that there is a relationship with monoamine even in mental disorders which inhibit the development of character and personality and developmental disabilities. For example, there are reports that there is a correlation between high levels of dopamine metabolites in schizophrenia (Siever, L. J., F. Amin, et al. (1993). Am J Psychiatry 150(1): 149-51), attention deficit hyperactivity disorder (ADHD), and dopamine metabolites (Gerra, G., C. Leonardi, et al. (2007). J Neural Transm 114(12): 1637-47). In addition, there are reports that there is a correlation between polymorphisms in genes of the dopamine receptor system (Lynn, D. E., G. Lubke, et al. (2005). Am J Psychiatry 162(5): 906-13), and polymorphisms in genes of the serotonin production system, receptor system, and metabolic system (Ribases, M., J. A. Ramos-Quiroga, et al. (2009). Mol Psychiatry 14(1): 71-85).

Furthermore, it has also been pointed out that there is a relationship between dopamine metabolite amounts and depressed patients with a history of alcohol dependency (Sher, L., M. A. Oquendo, et al. (2003). Neuropsychopharmacology 28(9): 1712-9). Further, it is understood that, even in neurodegenerative diseases such as Alzheimer's and Parkinson's disease associated with personality disorders, there is a relationship between quantitative anomalies of neurotransmitters starting with monoamine, hormones, and immune system molecules, and character alteration. In particular, Parkinson's disease, which causes abnormalities in dopamine neurons, has been well-researched (Kaasinen, V., E. Nurmi, et al. (2001). Proc Natl Acad Sci USA 98(23): 13272-7).

Regarding testosterone in the blood, the following is understood.

Testosterone levels in the blood are believed to reflect risk-taking tendencies (Rebecca Reavis and William H. Overman, Behavioral Neuroscience, "Adult Sex Differences on a Decision-Making Task Previously Shown to Depend on the Orbital Prefrontal Cortex", Vol. 115, No. 1, 196-206 (2001)). Moreover, there are also data showing that, for dealers actually working at a hedge fund, when the level of testosterone in the blood is high, the profit and loss for that day becomes significantly better. This is considered to be because there is a link between a tendency to take risks (in the short term) and good results ("Endogenous steroids and financial risk taking on a London trading floor" J. M. Coates and J. Herbert, PNAS 2008 vol. 105 no. 16 6167-6172). It has been confirmed that the administration of testosterone to women lowers sensitivity to punishment and increases reward-dependent decision-making (Jack van Honk, Dennis J. L. G. Schutter, Erno J. Hermans, Peter Putman, Adriaan Tuiten, Hans Koppeschaar, "Testosterone shifts the balance between sensitivity for punishment and reward in healthy young women", Psychoneuroendocrinology (2004) 29, 937-943).

The administration of testosterone to women increases the frequency of fair negotiations (C. Eisenegger, M. Naef, R. Snozzi, M. Heinrichs, and E. Fehr, "Prejudice and truth about the effect of testosterone on human bargaining behavior" Nature 463, 356-359 (2010)). In the ultimatum game, subjects with high testosterone were more likely to reject a low offer (unfair distribution proposal) and make irrational decisions (Maurice Levi, Kai Li, Feng Zhang, "Deal or no deal: Hormones and the mergers and acquisitions game", Management science, vol. 56, No. 9, (2010), pp. 1462-1483).
<Ultimatum Game>

The distribution of money is performed between two parties, the "proposer" and the "receiver". The proposer determines a method for dividing a sum of money between two people, which is then proposed to the receivers. The receiver determines whether to accept or reject the proposal of the division method. If the receiver accepts, the money will be distributed as determined by the proposer. However, if the receiver rejects the proposal, the amount of money received by both the proposer and the receiver becomes zero. Despite the harm done to their own interests, many receivers reject unfair distribution proposals.

Testosterone acts to have an antagonistic effect (to promote dominance and competitiveness) to oxytocin which controls sociability and reliability. The administration of testosterone to women has been experimentally confirmed to cause a decrease in trust in people (Peter A. Bos, David Terburg, and Jack van Honk, "Testosterone decreases trust in socially naïve humans" PNAS Early Edition (2010)).

Young male CEOs had a high tendency to show agonism and dominance; however, this tendency is considered to derive from the high testosterone levels of young men (Maurice Levi, Kai Li, Feng Zhang, "Deal or no deal: Hormones and the mergers and acquisitions game", Management science, vol. 56, No. 9, (2010), pp. 1462-1483).

In competition between males, it is understood that testosterone increases in the winner, which is believed to encourage further success in other challenges and competitions. On the other hand, testosterone decreases in the loser, which encourages a withdrawal from competition. Further, in collaborative competition as a team, it is understood that the testosterone increase is larger for members of a winning team than for successful members within a team. This finding suggests a hormonal system evolved for collaborative competition (Jonathan Oxford, Davide Ponzi, David C. Geary, "Hormonal responses differ when playing violent video games against an ingroup and outgroup", Evolution and Human Behavior, 31, (2010) p. 201-209).

In these studies, since blood content or cerebrospinal fluid of neurotransmitters, hormones, and immune system molecules are collected, there is an extremely high degree of invasiveness, which is not convenient.

SUMMARY

It is desirable to provide an individual information determining method, an individual information determining program, and an individual information determining device for determining individual information of subjects easily and with minimal invasiveness.

According to an embodiment of the present application described above, there is provided an individual information determining method determining individual information of a subject based on one or a plurality of pieces of biomolecule information on obtained from the surface of the body surface. In this manner, it is possible to obtain the biomolecule information with minimal invasiveness. Furthermore, it is possible to easily determine individual information from these minimally invasive data.

In addition, it is preferable to determine the individual information of the subject based on one or a plurality of pieces of biomolecule data collected from the surface of the body surface of the subject and living activity data at the time of collection.

In addition, it is preferable that the living activity data be living activity classification data.

In this manner, it is possible to further add information relating to living activity data.

In addition, it is preferable that the biomolecule data on the surface of the body surface quantify the monoamines or the steroid hormones.

It is preferable that the monoamines be one or more types selected from monoamines, monoamine precursors, and monoamine metabolites. Further, as the monoamines, catecholamines and types of serotonin may be exemplified. Of these, it is more preferable that one or more types be selected from dopamine, L-dopa, adrenaline, noradrenaline, serotonin, and the like.

Also, it is preferable that the biomolecule data of the monoamines be biomolecule data of one or both of dopamine and L-dopa.

In addition, it is preferable that the biomolecule data of the steroid hormones be selected from one or more of types of cortisol, androgens, and estrogens. Of these, androgens are preferable, and, as the androgens, testosterone, dihydrotestoterone, dehydroepiandrosterone, and the like may be exemplified. Of these, testosterone is preferable.

In addition, it is preferable to determine a dopamine increase in living activities of sleep or exercise from dopamine biomolecule data on the surface of the body surface, or determine a dopamine increase or decrease in living activities of stress, recreation, or exercise from sleep data from the dopamine biomolecule data and living activity data.

In addition, it is preferable to determine temperament traits of pursuit of novelty, damage avoidance, compensation dependence, and persistent tendencies as well as character traits of self-orientation, cooperativeness, and self-transcendence from one or both of the dopamine biomolecule data on the surface of the body surface and the L-dopa biomolecule data on the surface of the body surface.

In addition, it is preferable to determine temperament traits of persistent tendencies as well as character traits of compensation dependence and cooperativeness based on the average values of the biomolecules from the dopamine biomolecule data on the surface of the body surface and the living activity data.

In addition, it is preferable to determine temperament traits of persistent tendencies and pursuit of novelty based on the biomolecule data of the ratio of (dopamine on the surface of the body surface/L-dopa on the surface of the body surface) from the biomolecule data on the surface of the body surface and the average values of the biomolecules from the living activity data.

It is preferable to determine the following (a) to (d) from the dopamine biomolecule data on the surface of the body surface and the living activity data.
(a) Based on sleep data, temperament traits of persistent tendencies and character traits of self-orientation. (b) Based on stress data, temperament traits of compensation dependence as well as character traits of self-orientation and self-transcendence. (c) Based on recreation data, temperament traits of persistent tendencies as well as character traits of self-orientation, cooperativeness, and self-transcendence. (d) Based on exercise data, temperament traits of damage avoidance and persistent tendencies as well as character traits of self-orientation, cooperativeness, and self-transcendence.

It is preferable to determine the following (a) to (d) from the L-dopa biomolecule data on the surface of the body surface and the living activity data.
(a) Based on sleep data, temperament traits of compensation dependence and character traits of cooperativeness. (b) Based on stress data, temperament traits of damage avoidance as well as character traits of self-orientation and cooperativeness. (c) Based on recreation data, temperament traits of pursuit of novelty and persistent tendencies as well as character traits of self-orientation and cooperativeness. (d) Based on exercise data, temperament traits of pursuit of novelty, compensation dependence, and persistent tendencies as well as character traits of cooperativeness and self-transcendence.

It is preferable to determine the following (a) to (d) from the biomolecule data of the ratio of (dopamine on the surface of the body surface/L-dopa on the surface of the body surface) from the biomolecule data on the surface of the body surface and the living activity data.
(a) Based on sleep data, temperament traits of persistent tendencies and character traits of self-orientation. (b) Based on stress data, temperament traits of damage avoidance as well as character traits of self-orientation, cooperativeness and self-transcendence. (c) Based on recreation data, character traits of self-orientation, cooperativeness, and self-transcendence. (d) Based on exercise data, temperament traits of pursuit of novelty, damage avoidance, and persistent tendencies.

Moreover, according to another embodiment of the present application described above, there is provided an individual information determining device provided with an analysis unit creating individual information of a subject based on one or a plurality of pieces of biomolecule data collected from the surface of the body surface of the subject and living activity data at the time of collection.

Furthermore, it is preferable that the individual information determining device be provided with a biomolecule collection unit on the surface of the body surface collecting biomolecule data on the surface of the body surface with minimal invasiveness, and an output unit outputting the individual information. In this manner, it is possible to collect biomolecules on the surface of the body surface with minimal invasiveness. In addition, it is possible to output the created individual information in image or audio format.

In addition, it is preferable that the individual information determining device be provided with a storage unit transmitting and receiving the biomolecule data on the surface of the body surface and the living activity data to and from the analysis unit and storing the data.

Moreover, according to still another embodiment of the present application described above, there is provided an electronic apparatus provided with an analysis unit creating individual information of a subject based on one or a plurality of pieces of biomolecule data collected from the surface of the body surface of the subject and living activity data at the time of collection. It is possible to acquire and use the individual information of the subject.

It is preferable that the electronic apparatus be an individual information determining device, an exercise device, a sleep-related device, a recreational device, an educational device, or an apparatus in which an operation causing a stress load takes place.

Moreover, according to still another embodiment of the present application described above, there is provided a program for causing a computer to execute a biomolecule data processing function, a living activity data processing function, and an analysis function of creating individual information.

Specifically, the biomolecule data processing function processes biomolecules collected by a biomolecule collection unit on the surface of the body surface as biomolecule data on the surface of the body surface. It is possible to obtain biomolecule data with minimal invasiveness.

In addition, the living activity data processing function processes living activities at the time of collection acquired from the living activity acquisition unit as living activity data. It is possible to change activities of daily living into data form.

In addition, the analysis function of creating individual information performs determination of individual information based on one or both of biomolecule data on the surface of the body surface and living activity data. (A) When the biomolecule data on the surface of the body surface relate to monoamines, temperament traits of pursuit of novelty, damage avoidance, and persistent tendencies, as well as character traits of self-orientation, cooperativeness, and self-transcendence are determined (B) When the biomolecule data on the surface of the body surface relate to testosterone, the tendency to be aggressive and dominant in living activities, the tendency to take risks, the compensation dependence tendency, and the tendency not to trust others are determined. In this manner, it is possible to create individual information specific to individuals.

According to the embodiments of the present application, it is possible to determine individual information for a subject easily and with minimal invasiveness.

Additional features and advantages are described herein, and will be apparent from the following Detailed Description and the figures.

BRIEF DESCRIPTION OF THE FIGURES

FIG. 5 is a diagram showing an example of conversion information (table) for converting individual information relating to temperament and character information based on biomolecule data on the body surface and living activity data. DA: dopamine, DOPA: L-dopa. ↑: large increase in biomolecules, or each individual information tendency becomes strong when the deterioration amount is small, that is, a positive correlation. ↓: small increase in biomolecules, or each individual information tendency becomes weak when the deterioration amount is large, that is, a negative correlation.

FIG. 6 is a diagram showing an example of a method of defining and classifying the personality, temperament, and character of an individual (questionnaire examination relating to temperament and character).

FIG. 8 is a diagram showing a correlation between temperament and dopamine/dopa average values in the embodiment of the present application.

FIG. 15 is a diagram showing a persistent tendencies correlation between character and dopamine (dopa) in the embodiment of the present application.

FIG. 21 is a diagram showing a correlation between changes of L-dopa on the skin and changes of psychological indicators (before and after comparison of highest blood pressure, before and after comparison of heart rate) in the embodiment of the present application.

FIG. 23 is mainly for analysis with a focus on biomolecules on the surface of the body surface (type, amount, quantity ratio).

FIG. 24 is mainly for analysis with a focus on biomolecules on the surface of the body surface (type, amount, quantity ratio) and living activities of a subject on the surface of the body surface.

DETAILED DESCRIPTION

Figure 1A:
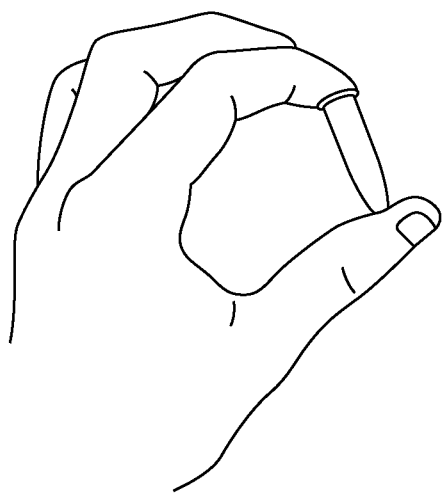
FIGS. 1A and 1B are diagrams showing examples of a method for transferring biomolecules to a solvent from the skin surface of the fingers.

Below, description will be given of preferable embodiments for carrying out the present application with reference to the drawings. Further, the embodiments described below are examples of typical embodiments of the present application and these should not be interpreted as narrowing the scope of the present application.

<1. Individual Information Determining Method>
 (1) Overview
 (2) Biomolecules
 (3) Biomolecule Data Processing on the Surface of the Body Surface
 (4) Living Activity Data Processing
 (5) Individual Information Analysis
(Determination Processing of Individual Information)
 (6) Individual Information Determining Flow
 (7) Conversion Information Creation Method
<2. First Embodiment: Biomolecule Data on the Body Surface/Monoamines>
 (1) Overview
 (2) Individual Information Determining Method Relating to the First Embodiment of the Present application
 (3) Individual Information Determining Method Based on One or Both of Dopamine Biomolecule Data and L-Dopa and Living Activity Data (A) to (E)

<3. Second Embodiment: Biomolecule Data on the Body Surface/Steroid Hormones>
  (1) Overview
  (2) Individual Information Determining Method Relating to the Second Embodiment of the Present application
<4. Individual Information Determining Device>
  (1) Biomolecule Data Processing Unit on the Body Surface
  (2) Living Activity Data Processing Unit
  (3) Individual Information Analysis Unit
  (4) Storage Unit
  (5) Output Unit
  (6) Electronic Apparatus
<5. Hardware Configuration of Embodiments of the Present application>

1. Individual Information Determining Method (1) Overview

In Japanese Unexamined Patent Application Publication No. 2010-226203, there is disclosed a biological information acquisition method including a process of acquiring biologically active substances (below, referred to as "biomolecules") from a living body from a surface of a body surface such as a finger or palm (below, referred to as "on the body surface") with the aim of sensing the biological information with high accuracy, as discovered by the inventors.

Furthermore, the present inventors focused on the relationship between individual information regarding temperament, character, and the like and biomolecules on the body surface, and, as a result of intensive research, discovered a relationship between the biomolecules and the individual information. Here, it was discovered that, by further adding the concept of living activities as a factor, it is possible to determine individual information with higher accuracy. For example, the table converting the individual information such as temperament, character, individuality, and the like and a conversion formula were applied to the biomolecules measured on the surface of the body surface or the quantity ratio of the molecule groups, and, as a result, the individual information was determined. In the conversion, it is preferable to use living activity factors such as sleep, stress, recreation, exercise and the like.

In this case, the present inventors are considered as follows.

From the technologys of: Nilsson, T., S. Psychiatry Res 178(3): 525-30; Giegling, I., D. Moreno-De-Luca, et al. (2008). Am J Med Genet B Neuropsychiatr Genet 147(3): 308-15; Giegling, I., D. Moreno-De-Luca, et al. (2009). Neuropsychobiology 59(1): 23-7; Sadahiro, R., A. Suzuki, et al. Behav Brain Res 208(1): 209-12.2009; Nyman, E. S., A. Loukola, et al. (2009). Am J Med Genet B Neuropsychiatr Genet 150B(6): 854-65. 2009; Schosser, A., K. Fuchs, et al. World J Biol Psychiatry 11(2Pt2): 417-24; Sheldrick, A. J., A. Krug, et al. (2008). Eur Psychiatry 23(6): 385-9; Shibuya, N., M. Kamata, et al. (2009). Behav Brain Res 203(1): 23-6; Bodi, N., S. Keri, et al. (2009). Brain 132(Pt9): 2385-95; Takahashi, H., H. Matsui, et al. J Neurosci 30(49): 16567-72; Beaver, K. M., M. G. Vaughn, et al. (2010). Intelligence; Garcia, J. R., J. MacKillop, et al. PLoS One 5(11):e14162; Siever, L. J., F. Amin, et al. (1993). Am J Psychiatry 150(1): 149-51; Gerra, G., C. Leonardi, et al. (2007). J Neural Transm 114(12): 1637-47; Lynn, D. E., G. Lubke, et al. (2005). Am J Psychiatry 162(5): 906-13; Ribases, M., J. A. Ramos-Quiroga, et al. (2009). Mol Psychiatry 14(1): 71-85; Sher, L., M. A. Oquendo, et al. (2003). Neuropsychopharmacology 28(9): 1712-9; and Kaasinen, V., E. Nurmi, et al. (2001). Proc Natl Acad Sci USA 98(23): 13272-7, for example, it is understood that it is possible to define character using the amounts of neurotransmitters, hormones, and immune system molecules, which are representative examples of monoamines, in the blood and in the cerebrospinal fluid or using related polymorphisms in genes. However, collecting blood or cerebrospinal fluid has an extremely high degree of invasiveness. It is possible to investigate polymorphisms in genes with minimal invasiveness; however, polymorphisms in genes information may obtain information relating to innate temperament, which is not sufficient to perceive the maturation process of human growth or changes of character. A correlation has also been reported between actual dopamine metabolites and childhood trauma (Lee, R. and E. F. Coccaro J Neural Transm 117 (11): 1327-34).

Further, to begin with, individual temperament and character are considered as being regulated by the condition of connections of neural circuits. The connection conditions of neural circuits are regulated by neurotransmitters when looking at the connections between separate nerve cells, and the production system, endocrine system, receptor system, and metabolic system of the neurotransmitters are important. In addition, regarding the connectivity and maturity of the neural circuits as a whole, the influence of nerve growth factors or hormones, and immune system molecules is great, and the production system, endocrine system, receptor system, and metabolic system are important. In other words, by acquiring information relating to these molecules, it is considered possible to define the character of an individual.

Here, it is considered that the character appears to a greater extent in the individual information when there is some kind of action or some kind of stimulus. In other words, if it is possible to measure changes in the neurotransmitters, hormones, and immune system molecules occurring alongside some kind of action or some kind of stimulus, it is considered that it is possible to obtain data for judging character in more detail.

However, in practice, the changes were not understood in the method of investigating polymorphisms in genes. Further, measuring molecules in blood and cerebrospinal fluid and measuring changes in chronological order were very difficult.

Further, from the technologys of: Rebecca Reavis and William H. Overman, Behavioral Neuroscience, "Adult Sex Differences on a Decision-Making Task Previously Shown to Depend on the Orbital Prefrontal Cortex", Vol. 115, No. 1, 196-206 (2001); "Endogenous steroids and financial risk taking on a London trading floor" J. M. Coates and J. Herbert, PNAS 2008 vol. 105 no. 16 6167-6172; Jack van Honk, Dennis J. L. G. Schutter, Erno J. Hermans, Peter Putman, Adriaan Tuiten, Hans Koppeschaar, "Testosterone shifts the balance between sensitivity for punishment and reward in healthy young women", Psychoneuroendocrinology (2004) 29, 937-943; C. Eisenegger, M. Naef, R. Snozzi, M. Heinrichs, and E. Fehr, "Prejudice and truth about the effect of testosterone on human bargaining behavior" Nature 463, 356-359 (2010); Maurice Levi, Kai Li, Feng Zhang, "Deal or no deal: Hormones and the mergers and acquisitions game", Management science, vol. 56, No. 9, (2010), pp. 1462-1483; Peter A. Bos, David Terburg, and Jack van Honk, "Testosterone decreases trust in socially naïve humans" PNAS Early Edition (2010); Maurice Levi, Kai Li, Feng Zhang, "Deal or no deal: Hormones and the mergers and acquisitions game", Management science, vol. 56, No. 9, (2010), pp. 1462-1483; and Jonathan Oxford, Davide Ponzi, David C. Geary, "Hormonal responses differ when playing violent video games against an ingroup and outgroup", Evolution and Human Behavior, 31, (2010) p. 201-209, in both the biological sociology model and the psychological model, it is considered that testosterone plays an important role with respect to sociability.

Moreover, testosterone is considered to have an influence on decisions and behavior as follows.

For example, an influence relating to risk taking behavior (Rebecca Reavis and William H. Overman, Behavioral Neuroscience, "Adult Sex Differences on a Decision-Making Task Previously Shown to Depend on the Orbital Prefrontal Cortex", Vol. 115, No. 1, 196-206 (2001); "Endogenous steroids and financial risk taking on a London trading floor" J. M. Coates and J. Herbert, PNAS 2008 vol. 105 no. 16 6167-6172; and Jack van Honk, Dennis J. L. G. Schutter, Erno J. Hermans, Peter Putman, Adriaan Tuiten, Hans Koppeschaar, "Testosterone shifts the balance between sensitivity for punishment and reward in healthy young women", Psychoneuroendocrinology (2004) 29, 937-943), an influence relating to fairness (Eisenegger, M. Naef, R. Snozzi, M. Heinrichs, and E. Fehr, "Prejudice and truth about the effect of testosterone on human bargaining behavior" Nature 463, 356-359 (2010); and Maurice Levi, Kai Li, Feng Zhang, "Deal or no deal: Hormones and the mergers and acquisitions game", Management science, vol. 56, No. 9, (2010), pp. 1462-1483), an influence relating to aggressive and dominant tendencies, as well as trust (Peter A. Bos, David Terburg, and Jack van Honk, "Testosterone decreases trust in socially naïve humans" PNAS Early Edition (2010); and Maurice Levi, Kai Li, Feng Zhang, "Deal or no deal: Hormones and the mergers and acquisitions game", Management science, vol. 56, No. 9, (2010), pp. 1462-1483), an influence on competition and motivation as a team (Jonathan Oxford, Davide Ponzi, David C. Geary, "Hormonal responses differ when playing violent video games against an ingroup and outgroup", Evolution and Human Behavior, 31, (2010) p. 201-209), and the like.

In other words, it is considered that investigating the level of testosterone in the blood makes it possible for a person to grasp their own tendency to be aggressive and dominant, tendency to take risk, compensation dependence tendency, tendency to seek fairness, tendency to trust others, and the like, and to apply this to self-management and the like to reduce irrational decision-making. In addition, it is considered that this may be applied to the selection of promising traders for a particular day, facilitation of team activities, motivation management, and the like.

However, typical methods involve collecting blood and are thus invasive. Consequently, the use thereof is substantially difficult in everyday living because the methods are not available other than to qualified physicians. Recently, in order to reduce the invasiveness, the collection of saliva as an alternative to blood has also been performed; however, the psychological burden is great and this is not realistic.

With respect to the current situation and issues, the possibility of using biomolecules on the surface of a body surface obtained easily and with minimal invasiveness to determine individual information such as character and temperament as in the present application was completely unexpected. Furthermore, it was also unexpected that it would become easier to determine the individual information by focusing on living activities.

(2) Biomolecules

The biomolecules used in the present application are not specifically limited. For example, steroid hormones, monoamines, peptides and the like; and precursors, metabolites, and the like thereof may be exemplified. The steroid hormones include cortisols, androgens and estrogens. In addition, the monoamines include catecholamines and the like. The peptides include growth hormones and the like. The biomolecules, as shown in Table 1, are already understood to have a relationship in combination with bio-information. As the bio-information, in addition to information concerning the stress and emotions, the menstrual cycle, the effects of exercise, and the like, for example, sleepiness (level of wakefulness), state of health, circadian rhythms (bio-rhythms) and the like may be exemplified. However, it is not well understood whether there is an unambiguous relationship with the individual information of the present application.

TABLE 1

| Biological Information | Biologically Active Substances | |
|---|---|---|
| Stress | Steroid hormones | Cortisol, corticosterone, cortisone |
| | Peptides | NPY |
| Emotion (aggressiveness) | Steroid hormones | Testosterone, dihydrotestosterone (DHT), dehydroepiandrosterone (DHEA) |
| Emotion (excitement, fear, anger) | Catecholamine | Noradrenaline (norepinephrine), adrenaline (epinephrine) |
| Emotion (recreation) | Catecholamine | Dopamine |
| | Peptides | Endorphins |
| Emotion (unease) | Monoamines | Serotonin |
| | Peptides | Oxytocin, vasopressin, galanin |
| Sleepiness (level of wakefulness) | | Melatonin |
| Menstrual Cycle | Steroid hormones | Estrone (E1), estradiol (E2), estriol (E3) |

The biologically active substances shown in Table 1 are examples.

Besides these, as catecholamines, for example, metanephrine and normetanephrine, 3-methoxy-4-hydroxymandelic acid, 3-methoxy-4-hydroxyphenylglycol, 3,4-dihydroxymandelic acid, 3,4-dihydroxyphenylglycol, 3,4-dihydroxyphenyl acetic acid, 3-methoxy-tyramine, homovanillic acid, 5-hydroxyindoleacetic acid, vanillylmandelic acid, and the like may be bio-information indicators.

In addition, as steroid hormones, for example, aldosterone and deoxycorticosterone, androstenedione, progesterone, 11-deoxycorticosterone, pregnenolone, 11-deoxycortisol, 17-hydroxyprogesterone, 17-hydroxypregnenolone, cholecalciferol (vitamin D), and the like may be bio-information indicators.

Furthermore, as the biologically active substances acting as bio-information indicators, the following examples may be exemplified.

As hypophysiotropic hormones, corticotropin releasing hormones (CRH) and growth hormone releasing hormones (GRH), somatostatin (growth hormone secretion inhibiting hormones), gonadotropin-releasing hormone (GnRH), prolactin-releasing hormone (PRH), prolactin-inhibiting hormone (PIH), thyrotropin-releasing hormone (TRH), thyroid stimulating hormone (TSH) and the like.

As thyroid hormones, thyroxine and triiodothyroxine and the like.

As various hormones and neurotransmitters, chromogranin A and adrenocorticotropic hormones (ACTH), luteinizing hormone (LH), insulin-like growth factor I (IGF-I), prolactin, pro-opiomelanocortin (POMC), oxytocin, α-melanocyte-stimulating hormones (α-MSH), glucagon, ghrelin, gallanin, motilin, leptin, gastrin, cholecystokinin, selectins, activin, inhibin, neurotensin, bombesin, substance P, angiotensin I, II, enkephalin, orexin A, B, anandamide, acetylcholine, histamine, glutamate, glycine, aspartic acid, pyrimidine, adenosine, adenosine triphosphate (ATP), GABA, FMRF amide, peptide YY, agouti-related peptide (AgRP), cocaine- and amphetamine-regulated transcript product (CART), calcitonin gene-related peptide (CGRP), glucagon-like peptide 1, 2 (GLP-1,2), vasoactive intestinal peptide (VIP), gastrin-releasing peptide (GRP), melanin-concentrating hormone (MCH), and the like.

Of these, monoamines are preferable as the biomolecules used in the present application. As the monoamines, one or more types selected from monoamines, monoamine precursors and monoamine metabolites are preferable. Further, as the monoamines, one or both of catecholamines and serotonin are preferable. More preferably, one or more types selected from dopamine, L-dopa, adrenaline, noradrenaline, serotonin and the like are preferable.

In addition, steroid hormones are preferable as the biomolecules used in the present application. As the steroid hormones, one or more types selected from androgens such as testosterone and the like, and cortisols such as cortisol and the like are preferable. Of these, testosterone is preferable.

(3) Biomolecule Data Processing on the Surface of the Body Surface

Description will be given of the process for acquiring biomolecules of a subject for data processing in the body surface biomolecule data processing unit 2 and obtaining results (data) therefrom.

The acquisition of biomolecule data on the surface of the body surface may use a method in which a measurement device such as a bio-information acquisition apparatus (for example, Japanese Unexamined Patent Application Publication No. 2010-266203) is used and in which signals are transmitted and received wirelessly or through a wire to and from the body surface biomolecule data processing unit 2.

In addition, for example, a method in which the measurement results of the body surface biomolecules of the subject are input by an input method such as a mobile terminal, a keyboard, or the like by the subject or someone else, and in which signals are transmitted and received wirelessly or through a wire to and from the body surface biomolecule data processing unit 2 may be used.

In more detail, description will be given of the process for collecting and measuring one or a plurality of biomolecules from the body surface of a subject and obtaining results (data) therefrom.

For example, biomolecules existing in the body surface due to secretion or permeation may be measured in a measurement apparatus by placing a solvent having affinity with biomolecules in contact with the body surface and taking the biomolecules into the solvent. Further, the measurement apparatus may be placed in direct contact with the body surface or measurement may be performed indirectly through a seal or a solid material surface or the like placed in contact with the body surface.

The solvent used may be water or any of various organic solvents, and it is preferable to use a solvent such as those used in cosmetics, for example, ethanol and water, or 1,3-butanediol and water. The body surface to be contacted with the solvent is not particularly limited; however, the skin surface of the finger or the palm is convenient.

Figure 1B:

As a specific example of acquiring biomolecules from the body surface, biomolecules are acquired from the skin of the finger with reference to FIGS. 1A and 1B.

The body surface is placed in contact with the solvent in a microtube, whereby the biomolecules present on the body surface may be taken into the solvent by a physical method such as shaking, applying negative pressure and pressing force, and the like.

For example, as shown in FIG. 1A, the opening of the upper part of the microtube holding the solvent touches the tip of the index finger, and the solvent is shaken so as to come into contact with the skin. In this manner, it is possible to take the biomolecules on the skin into the solvent in the microtube. The solvent containing biomolecules is analyzed.

In addition, as shown in FIG. 1B, the protruding part of the microsyringe holding the solvent touches the tip of the index finger, and the solvent is set so as to come into contact with the skin. Then, negative pressure is applied in the syringe with a piston movement and contact is maintained for one minute. In this manner, it is possible to carry out intake of the biomolecules on the skin with a high intake rate to the solvent in the syringe. The solvent containing biomolecules is analyzed.

Figure 2:
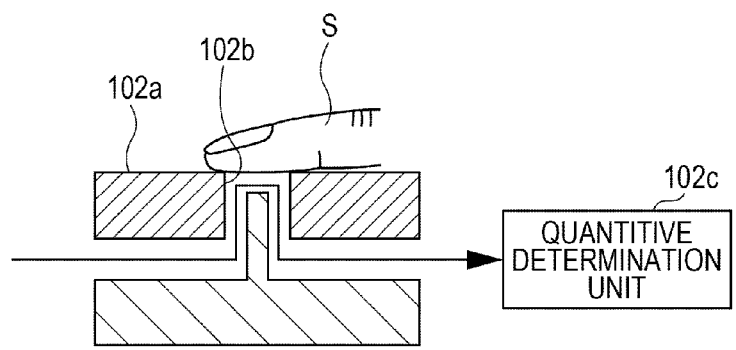
FIG. 2 is a diagram showing an example of a collection unit of an apparatus for acquiring and measuring biomolecules from the skin surface of the fingers.

Further, as shown in FIG. 2, the tip of the index finger S touches the opening 102b of the collection unit surface 102a. The solvent is transported in the arrow direction, at which point the solvent comes into contact with the skin. In this manner, it is possible to take biomolecules on the skin into the solvent, which are then transported to the quantitative determination unit 102c, and the solvent containing the biomolecules is analyzed.

In addition, the measurement may be performed by pressing the body surface and taking the attached biomolecules into the solvent.

The quantitative determination of the biomolecules on the body surface may be performed using a common method, for example, chromatography (HPLC or the like), enzyme immunoassay, radioimmunoassay or the like. It is also possible to perform quantitative determination by using a surface plasmon sensor (SPR) or a quartz crystal microbalance sensor (QCM). Such methods may be used alone or in combination.

More specifically, for example, there are biochemical techniques and immunoassays that perform quantitative determination using absorptivity, fluorescence and color development according to structural changes of a substrate using enzymes and antibodies. Further, there is a method of performing quantitative determination of the enzymes and antibodies in combination with another sensor; for example, combination with a surface plasmon resonance (SPR) sensor, a semiconductor (FET) sensor, or an electrochemical sensor. Further, a method of performing quantitative determination from the electrification characteristics and mass spectrometry of the target biomolecules, as well as a method of combining chromatography and electrophoresis may be exemplified.

According to the (measurement) method of collecting the biomolecules on the surface of the body surface in this manner, it is possible to determine the quantity of the biomolecules easily and with minimal invasiveness by acquiring the biologically active substances from the surface of the body surface such as the finger or the palm.

Then, the types of the biomolecules on the surface of the body surface and the respective quantities thereof (for example, refer to FIG. 4) as well as the results of the amount of variation of the biomolecules in accordance with the activities may be more appropriately obtained. The results of the biomolecules present on the surface of the body surface are transmitted to the body surface biomolecule data processing unit 2 and made into respective body surface biomolecule data for each biomolecule. Then, in the individual information analysis unit 1, the body surface biomolecule data may be linked in parallel to the living activity data as described below, and any one kind of data may be classified and included. In addition, the inclusion (classifying) of living activity data is preferable from the point of ease of searching at the time of determining the individual information and upon data management.

(4) Living Activity Data Processing

Description will be given of the process in which, in the living activity data processing unit 3, the living activities of a subject for data processing are acquired, and results (data) are obtained therefrom.

The acquisition of the living activity data may use a method in which input is performed using an input method such as a mobile terminal, a keyboard, or the like by the subject or someone else and in which signals are transmitted and received wirelessly or through a wire to and from the living activity data processing unit 3. In addition, the acquisition of the living activity data may use a method in conjunction with schedule management software, or a method in conjunction with the change curve of the quantity of biomolecules (biological clock).

In addition, the acquisition of the living activity data may use a method in which a device for identifying living activities is used and in which signals are transmitted and received wirelessly or through a wire to and from the living activity data processing unit 3. As the device for identifying living activities, for example, a gyro sensor, an acceleration sensor, an optical sensor, a watch, a heart rate monitor, a blood pressure monitor, a miniature camera and the like may be exemplified.

The use of devices for identifying movement such as a gyro sensor, an acceleration sensor, and the like is convenient for the acquisition of living activity data of exercise. Moreover, the use of optical sensors and watches is convenient for the acquisition of long-term living activity data over time since they allow easy identification of regular living patterns according to light detection and the time, as well as allowing easy identification of the time for body surface biomolecule data acquisition. The use of devices for identifying a blood flow state such as a heart rate monitor and a blood pressure monitor is convenient for the acquisition of living activity data such as eating, sleep, exercise, work, study, and the like. Further, the use of devices such as miniature cameras for identifying the state of living activities is convenient for the acquisition of living activity data such as recreation, eating, medication, exercise, work, study, and the like.

Then, in the living activity acquisition unit 103, the results of the living activity states of the subject at the time of biomolecule data collection are obtained. Then, the results of the living activities are transmitted to the living activity data processing unit 3 to become individual specific living activity data.

It is possible to set the living activity data as living activity classification data according to a classification reference such as one or both of the living activity state and period (year, month, day, hour, minute, second) and the like. In this manner, it is possible to make classifications for each specific group and to subdivide the living activity data. Therefore, it is possible to determine the individual information with greater accuracy.

For example, the living activity data are classified by actions such as medication, eating, exercise, sleep, recreation, work, study and the like from living activity states of the subject at the time of biomolecule data collection, and made into living activity classification data. In addition, with the start of a certain activity as a base point, it is possible to add "before", "during", and "after", for example, "before medication" and the like. Here, depending on the type of the living activity, as a guide, "before" roughly means "1 to 30 minutes before the start of the activity" and "after" roughly means "1 to 30 minutes after the end of the activity". In this manner, it is possible to obtain change values and the like resulting from the activity.

In addition, the living activity data may be classified by period from the periods (year, month, day, hour, minute, second) set arbitrarily or with a scheduled start time and end time, and made into living activity classification data. When scheduling, time setting or the like of a watch or suchlike may be used. In this manner, it is possible to obtain average values or the like for a specific time, over a specific or predetermined period of days, weeks, or months.

In addition, the living activity data may be classified by combining each living activity as described above and the period according to living activity state of the subject at the time of biomolecule data collection and the period (year, month, day, hour, minute, second), and made into living activity classification data.

Here, the living activity data may linked in parallel with the above-described body surface biomolecule data, or data classified into any one kind of data and included in the individual information analysis unit 1.

(5) Individual Information Analysis (Determination Processing of Individual Information)

The respective data are transmitted from the body surface biomolecule data unit 2 to the individual information analysis unit 1. In this manner, determination of the individual information is performed based on the body surface biomolecule data.

Preferably, the respective data are transmitted from the body surface biomolecule data unit 2 and the living activity data processing unit 3. In this manner, determination of the individual information is performed based on the body surface biomolecule data and living activity data.

It is possible to process the biological biomolecule data and living activity data in the following manner.

For example, normal values of specific body surface biomolecules, normal values of the quantity ratio of the two or more body surface biomolecules, change values (change amounts) of a set period of the body surface biomolecules according to living activities (activities and stimuli), and the like may be exemplified.

As normal values of specific body surface biomolecules, for example, the amount of dopamine upon awakening or a measurement value at a set time, an average value for a predetermined period, a daily average value, or the like may be exemplified.

As the normal values of the quantity ratio of the two or more body surface biomolecules, for example, the value of the ratio of dopamine and dopa upon awakening, a daily average value, or the like may be exemplified.

As change values of a set period of the body surface biomolecules according to living activities (activities and stimuli), the change values of dopamine or the ratio of dopamine and dopa before and after sleep or before and after exercise, or the like may be exemplified.

In addition, the daily average values are calculated from the results of the body surface biomolecules measured in one day. More preferably, the values are calculated from regular data of many living activities. In this manner, it is possible to calculate the stable individual daily average.

In addition, information relating to biorhythms is acquired and a change curve of the quantity of biomolecules showing changes over time is created based on the changes over time of the quantity of biomolecules. These data may be stored. This is used as a molecular timetable for estimating the circadian rhythm and it is also possible to acquire living activity information (data) based on the molecular timetable. As such biomolecules, for example, body surface monoamines or nicotinamide metabolites, α-amylase derived with minimal invasiveness (Japanese Unexamined Patent Application Publication No. 2009-34100), and the like may be exemplified. Further, for example, when L-dopa is used, it is possible to acquire the living activity information relating to before and after sleep, stress, recreation, exercise, and the like according to the before and after ratio of L-DOPA (for example, refer to FIG. 20).

Here, by applying the processed data from other such biomolecule data or the like of living bodies to conversion information such as a table or a conversion formula, determination of the individual information is performed and the individual information is created.

The created individual information may be output by the output section 105, or may be stored in the storage unit 104.

Description will be given of the process in which the individual information is determined from the above-described results (data).

In the individual information analysis, conversion information such as a table or a conversion formula for converting the temperament information and the character information is stored in the individual information analysis unit 1 and the storage unit 104. This conversion information is for converting the single or plural biomolecules measured on the skin, or the quantity or quantity ratio of molecule groups into temperament information and character information.

Figure 26:
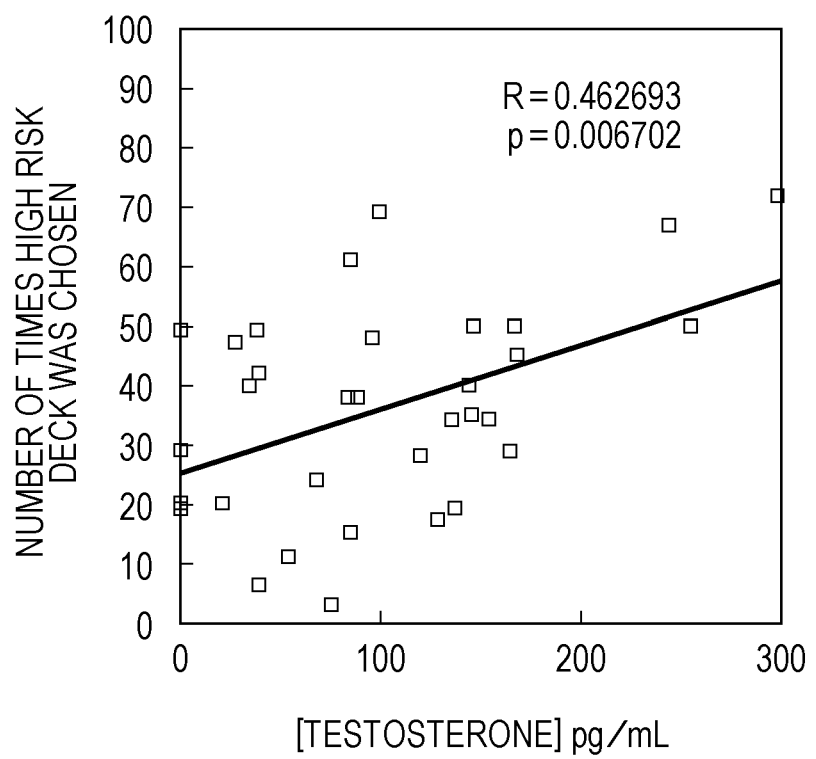
FIG. 26 is a diagram showing a correlation relationship between a risk taking ratio and testosterone on the skin of another embodiment of the present application.

In relation to the conversion information, for example, the list of FIG. 5 and the filings of monoamines such as the correlation data as shown in FIGS. 7 to 18, FIG. 21, and FIG. 22 may be exemplified. Further, the filings of steroid hormones such as the correlation data as shown in FIG. 26 and Table 2 may be exemplified. However, the embodiments of the present application are not limited thereto.

Description will be given below of an example of the filings of monoamines.

For example, in the dopamine average values (refer to FIG. 7), dopamine average value: compensation dependence (positive), DA average value: cooperativeness (positive), DA average value: persistent tendencies (negative).

Further, in the DA average values/L-dopa average values (refer to FIG. 8), DA average value/L-DOPA average value: pursuit of novelty (positive), DA average value/L-DOPA average value: persistent tendencies (negative).

In addition, in the dopamine (L-dopa) and character (pursuit of novelty), DA average value/L-DOPA average value: pursuit of novelty (positive), DA [before/after recreation]: pursuit of novelty (positive), L-DOPA [before/after exercise]: pursuit of novelty (negative).

In the dopamine (L-dopa) and character (damage avoidance), L-DOPA [before/after stress]: damage avoidance (positive), DA [before/after exercise]: damage avoidance (negative), exercise [ΔDA average value/ΔL-DOPA average value]: damage avoidance (negative).

In the dopamine (L-dopa) and character (compensation dependence), L-DOPA [before/after sleep]: compensation dependence (negative), DA average value: compensation dependence (positive), L-DOPA [before/after exercise]: compensation dependence (positive), DA [before/after stress]: compensation dependence (negative).

In the dopamine (L-dopa) and character (persistent tendencies), L-DOPA [before/after recreation]: persistent tendencies (negative), L-DOPA [before/after exercise]: persistent tendencies (positive), DA [before/after sleep]: persistent tendencies (positive), DA [before/after recreation]: persistent tendencies (negative), DA [before/after exercise]: persistent tendencies (negative), exercise [ΔDA/ΔL-DOPA]: persistent tendencies (negative).

In the dopamine (L-dopa) and character (self-orientation), DA average value: self-orientation (negative), DA average value/L-DOPA average value: self-orientation (negative).

In the dopamine (L-dopa) and character (self-orientation), DA [before/after sleep]: self-orientation (negative), DA [before/after exercise]: self-orientation (positive), L-DOPA [before/after stress]: self-orientation (negative), DA [before/after stress]: self-orientation (positive), stress [ΔDA/ΔL-DOPA]: self-orientation (positive), DA [before/after recreation]: self-orientation (positive), recreation [ΔDA/ΔL-DOPA]: self-orientation (positive).

In the dopamine (L-dopa) and character (cooperativeness), DA average value: cooperativeness (positive), L-DOPA [before/after stress]: cooperativeness (positive), L-DOPA [before/after sleep]: cooperativeness (negative), recreation [ΔDA/ΔL-DOPA]: cooperativeness (positive), L-DOPA [before/after exercise]: cooperativeness (positive), DA [before/after sleep]: cooperativeness (negative), DA [before/after recreation]: cooperativeness (positive), DA [before/after exercise]: cooperativeness (positive).

In the dopamine (L-dopa) and character (self-transcendence), L-DOPA [before/after exercise]: self-transcendence (negative), DA [before/after recreation]: self-transcendence (negative), DA [before/after stress]: self-transcendence (negative), stress [ΔDA/ΔL-DOPA]: self-transcendence (negative).

In addition, in the psychological indicators of dopamine (L-dopa) and catecholamines, DA [before/after load]: maximum systolic blood pressure [before/after load] (positive), L-DOPA DA [before/after load]: heart rate [before/after load] (positive), DA average value: diastolic blood pressure (positive).

As an example, certain subjects manually input biomolecule data of dopamine on the body surface before and after exercise and whether the time of collection was before or after exercise.

As a further example, certain subjects measure biomolecules on the body surface before and after exercise in the body surface biomolecule collection unit 102. At this time, the living activity acquisition unit 103 detects the peaks of a single or a plurality of biomolecules during living activities and calculates the amounts thereof (change amounts) from the dopamine peaks therein.

As a further example, certain subjects measure biomolecules on the body surface in the body surface biomolecule collection unit 102 and calculate the biomolecule amounts (change amounts) as described above. Thereafter, it is possible to acquire living activity data from the biomolecule data based on a molecule timetable.

The data are transmitted to the body surface biomolecule data processing unit 2 or the body surface data biomolecule processing unit 2 and the living activity data processing unit 3.

Furthermore, the above-described data are transmitted to the individual information analysis unit 1.

First, for example, from the column "exercise" of the dopamine (DA) table of FIG. 5, the individual information analysis unit 1 selects "damage avoidance" from temperament and "self-orientation" and "cooperativeness" from character. Then, when the dopamine amount after exercise is high with respect to the dopamine amount before exercise, the individual information analysis unit 1 determines from FIG. 5 that the temperament has low damage avoidance and the character has high self-orientation and cooperativeness.

Figure 12:
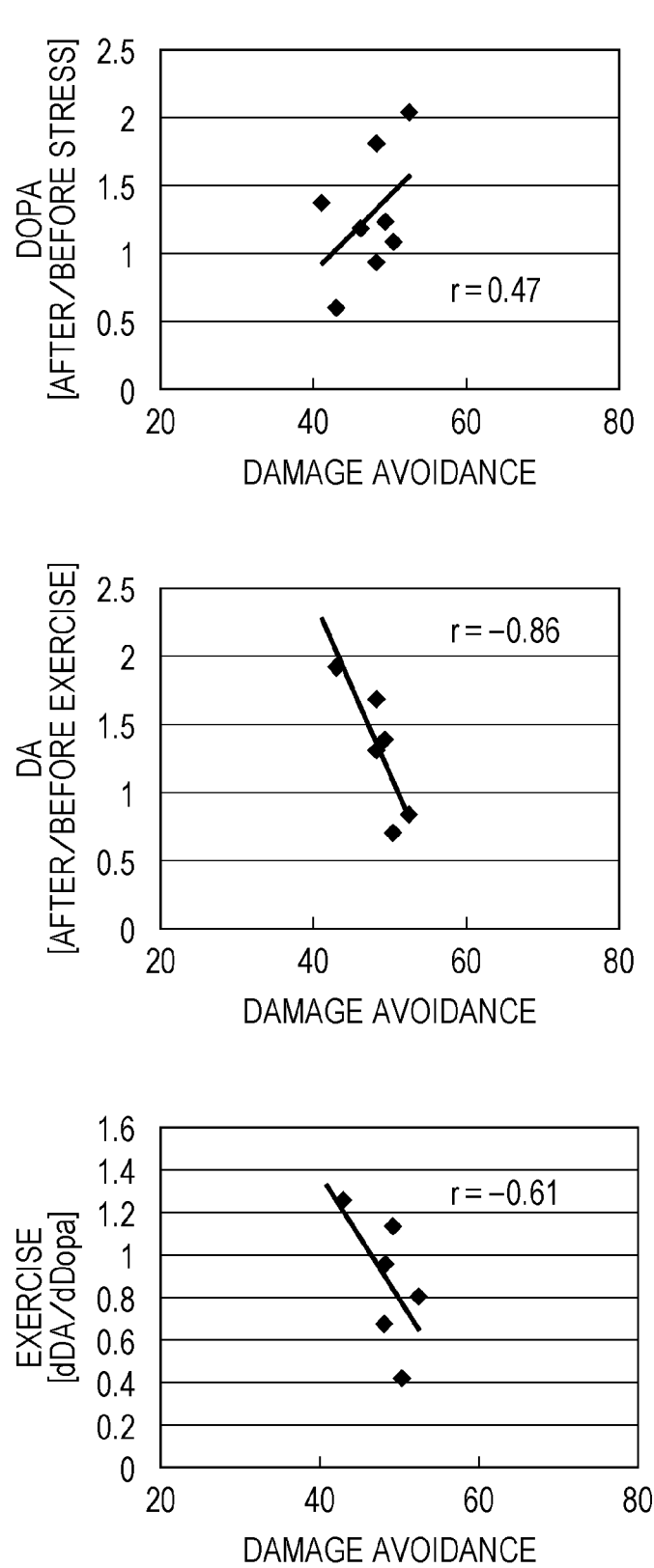
FIG. 12 is a diagram showing a damage avoidance correlation between character and dopamine (dopa) in the embodiment of the present application.
Figure 16:
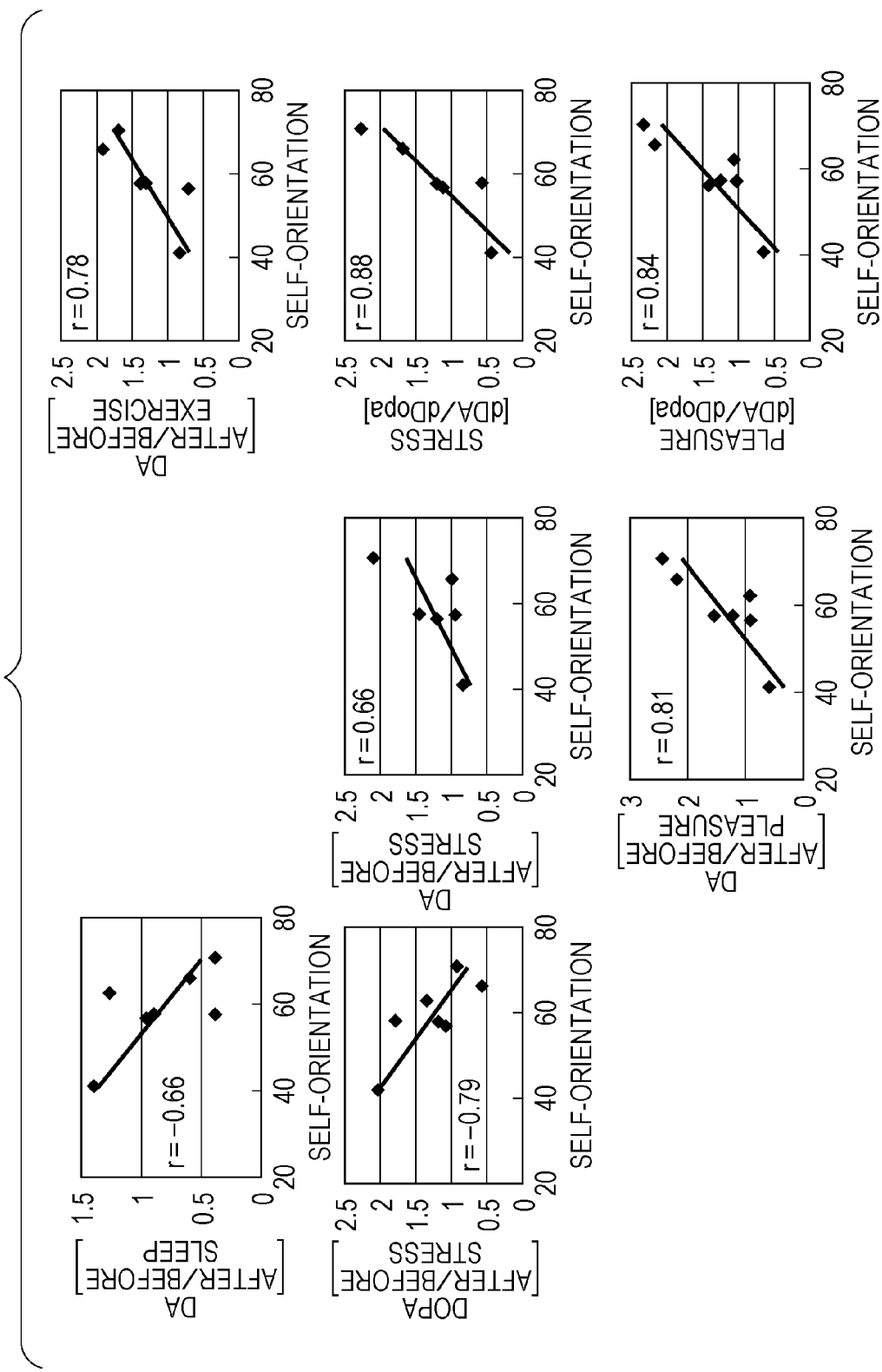
FIG. 16 is a diagram showing a self-orientation correlation between character and dopamine (dopa) in the embodiment of the present application.
Figure 17:
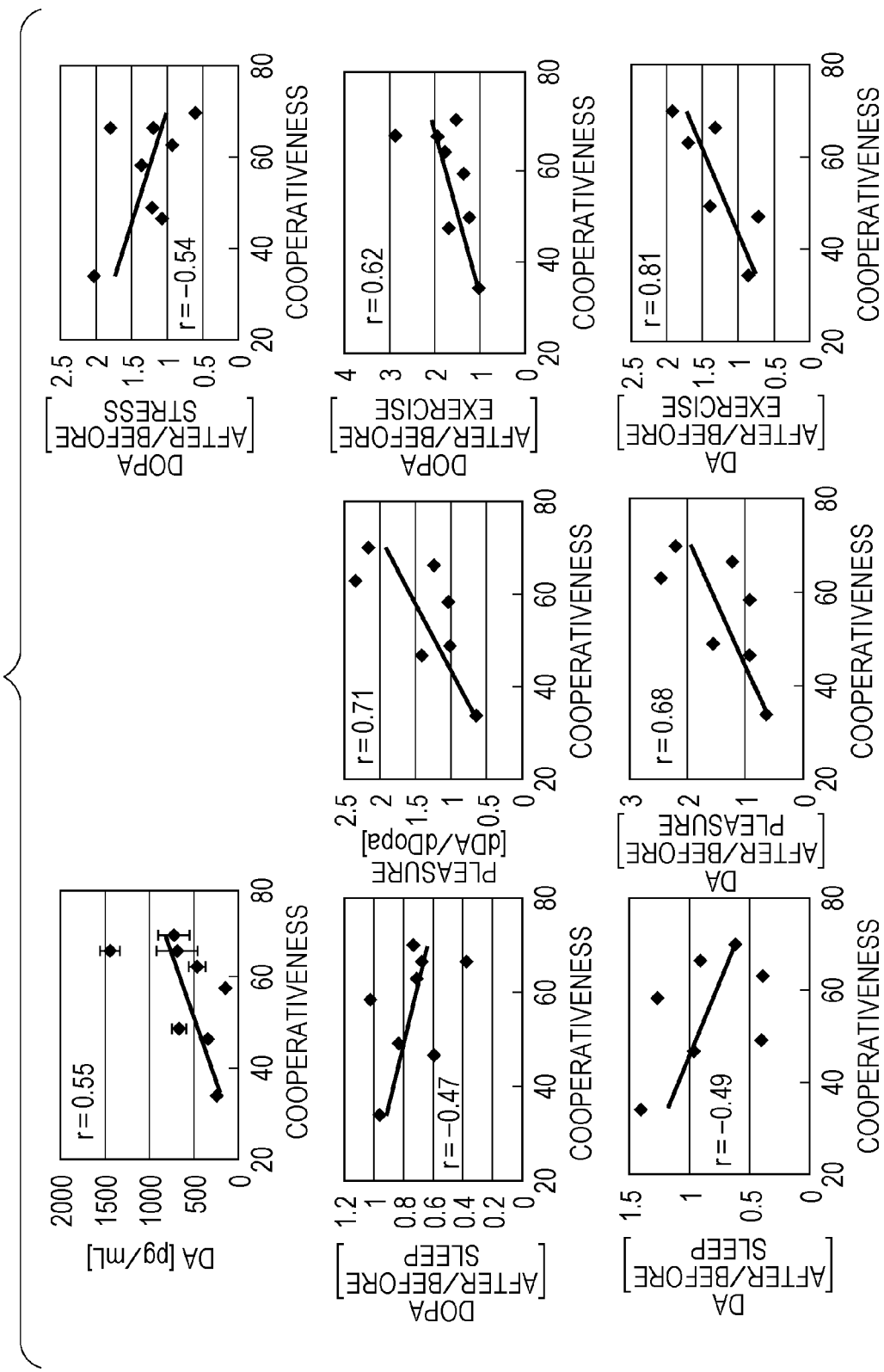
FIG. 17 is a diagram showing a cooperativeness correlation between character and dopamine (dopa) in the embodiment of the present application.
Figure 18:
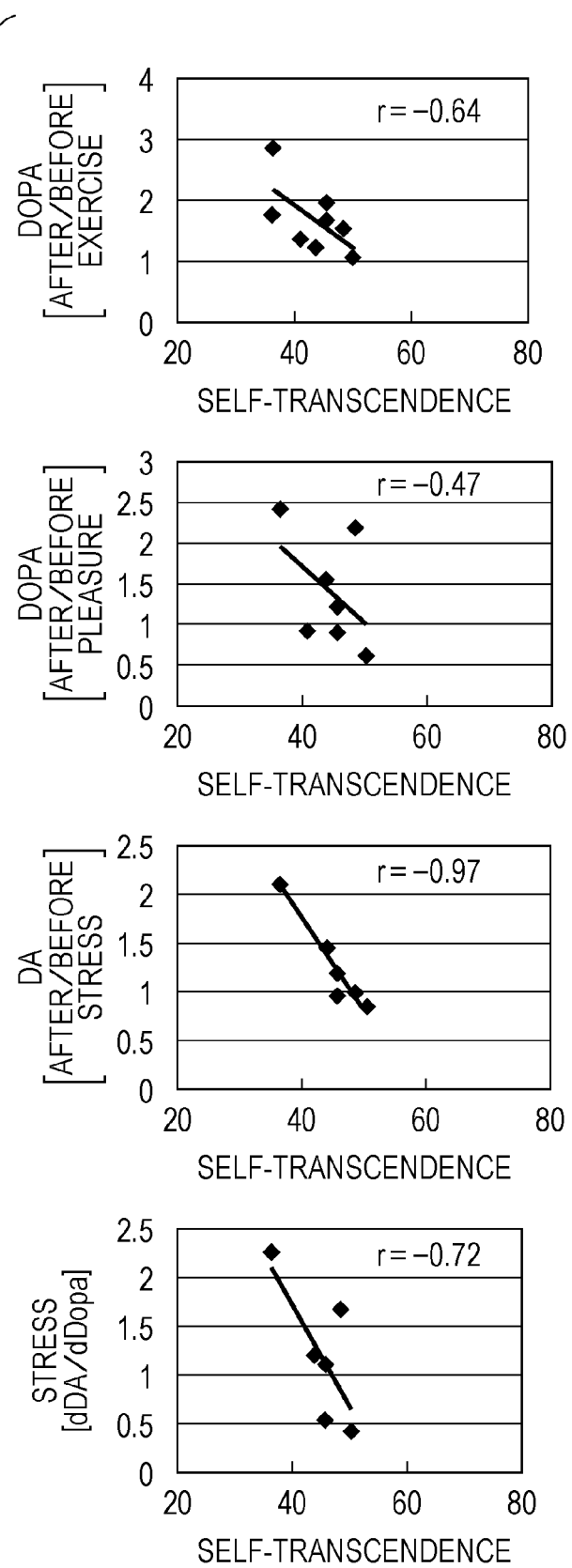
FIG. 18 is a diagram showing a self-transcendence correlation between character and dopamine (dopa) in the embodiment of the present application.

Next, the "damage avoidance" file of FIG. 12, the "self-orientation" file of FIG. 16, and the "cooperativeness" file of FIG. 17 are selected. Furthermore, the "after exercise/before exercise" file in each file is selected.

In addition, in the case of the "damage avoidance" file of FIG. 12, when the dopamine amount after exercise is higher than the dopamine amount before exercise, for example, when "after/before"=2, it is determined that the temperament has low damage avoidance of around 40%. Further, conversely, when the dopamine amount after exercise is lower than the dopamine amount before exercise, it is determined that the temperament has high damage avoidance. On the other hand, in the case of the "self-orientation" file of FIG. 16, when the dopamine amount after exercise is higher than the dopamine amount before exercise, for example, when "after/before"=2, it is determined that the character has high self-orientation of around 80%.

In addition, an example of the filings of steroid hormones will be described below.

For example, for testosterone and the risk taking ratio (refer to Table 2 and FIG. 26), testosterone concentration: risk taking ratio (positive). Moreover, for cortisol and the risk-taking ratio (refer to Table 2), cortisol concentration: risk taking ratio (positive).

(6) Individual Information Determining Flow

Figure 3:
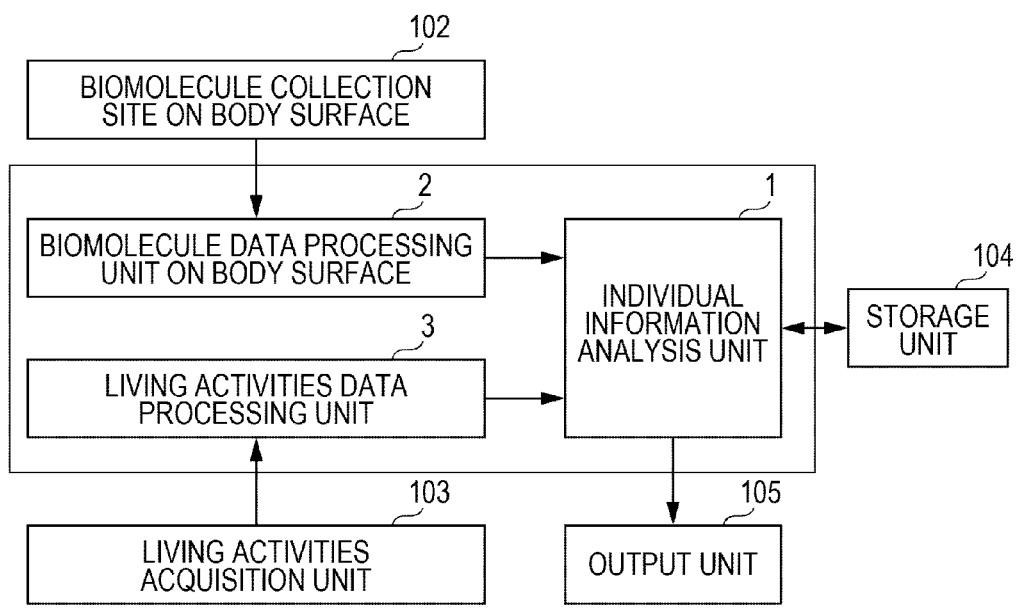
FIG. 3 is a block diagram showing a configuration of an individual information method (individual information apparatus) relating to the present application.

Referring to FIG. 3, an example of the individual information determining flow of an embodiment of the present application will be described in the following [Step 1] to [Step 6]. The individual information determining flow of an embodiment of the present application is not particularly limited thereto.

[Step 1]: The measurement results of the biomolecules on the body surface of the body surface biomolecule collection unit 102 are transmitted to the body surface biomolecule data processing unit 2, and become body surface biomolecule data (specification of the substance (identification) and the amount thereof). As the specified (identified) and quantified substance, for example, dopamine, L-dopa, testosterone, cortisol, and the like may be exemplified.

[Step 2]: In addition, the measurement results of the living activity acquisition unit 103 are transmitted concurrently or separately to the living activity data processing unit 3 to become living activity data, and, as appropriate, living activity classification data according to a classification standard.

[Step 3]: Then, the body surface biomolecule data and the living activity data are transmitted concurrently or separately to the individual information analysis unit 1, whereby the body surface biomolecule data and the living activity data are linked in parallel, or one set of data is classified and included.

At this time, such data may be stored in the storage unit 104.

[Step 4]: Next, in the individual information analysis unit 1, the "body surface biomolecule data" and the "living activity data at this time" become combined data. In addition, the conversion information (for example, a conversion formula, a conversion table, or the like) corresponding to the "body surface biomolecule data and living activity data at this time" is selected from a conversion information file (data).

[Step 5]: Then, one or both of the "body surface biomolecule column" and the "living activity" column of the selected conversion information (for example, the case of the conversion table) are applied to one or both of the "biomolecule data" and the "living activity data" in the "body surface biomolecule data and living activity data at this time". Here, individual information (specifically, temperament, character, individuality, and the like) having a correlation is selected, and determined as individual information. The determined result is displayed.

[Step 6]: In addition, when there are correlation data in the conversion information file, the degree of tendencies of temperament, character, and the like are determined as a ratio (%) based on one or both of the "biomolecule data" and the "living activity data".

Further, it is also possible to input one or both of the body surface biomolecule data (measurement values of separate biomolecules) and the living activity (classification data) in the input method.

Furthermore, while storing the living activity at the time of collecting the body surface biomolecules, it is possible to perform setting in advance so as to automatically start the individual information processing when a predetermined period has passed since the classification standard was applied and the data were accumulated.

In addition, it is possible to set the individual information processing to automatically start after the gathering of the biomolecule data and the living activity data has been completed by using the input method in advance at the time of collection, or to perform direct input with the input method.

In addition, as described above, since it is possible to obtain living activity information based on the body surface biomolecule data, the above [Step 2] to [Step 3], or [Step 2] to [Step 4] may be skipped. Below, an example is shown.

[Step 1a]: The measurement results of the body surface biomolecules of the body surface biomolecule collection unit 102 are transmitted to the body surface biomolecule data processing unit 2, and become body surface biomolecule data (specification of the substance (identification) and the amount thereof).

At this time, such data may be stored in the storage unit 104.

[Step 2a]: Next, in the individual information analysis unit 1, conversion information (for example, a conversion formula, a conversion table, or the like) corresponding to the "body surface biomolecule data" is selected from a conversion information file (data).

[Step 3a]: Then, individual information (specifically, temperament, character, individuality, and the like) having a correlation to the "body surface biomolecule data" in the selected conversion information (for example, the case of correlation data) is selected based on the "biomolecule data", and determined as individual information. Further, the degree of tendencies of temperament, character, and the like is determined as a ratio (%). The determination results are displayed.

(7) Conversion Information Creation Method

In addition, regarding the creation method of the conversion information, description will be given below; however, this is an example and is not limiting.

Data are acquired from a test subject in order to create conversion information with typical techniques to define and classify individual information of individual temperament, character, and the like (for example, refer to FIG. 6), such as the questionnaire method, a performance test temperament, a table corresponding to specific stimuli, or a game method such as the ultimatum game or the Iowa gambling task. The body surface biomolecules at the time of the living activity of the previously described test subject of the conversion information creation are measured. In this manner, the body surface biomolecule data and living activity data of the test subject of the conversion information creation are obtained. The correlation relationship between the results obtained by the questionnaire method or the like of the test subject of the conversion information creation, and one or both of the biomolecule data and the living activity data will be looked at. From this correlation relationship, conversion information is obtained.

For example, the filings as shown in FIGS. 7 to 18 are performed, and the conversion information as in FIG. 5 is obtained from the results. Such filings may be performed using biostatistics (multivariate analysis or the like).

Furthermore, it is possible to store the results obtained by the questionnaire method and the like in the storage unit 104. Then, as described above, by inputting and transmitting the respective data, the correlation relationship in the individual information analysis unit 1, the body surface biomolecule data processing unit 2 and the living activity data processing unit 3 is determined, and the conversion information may be created therefrom.

At this point, for example, based on the correlation coefficient r, it is possible to present the "accuracy" of the individual information determination. It is possible to perform output in a predetermined range, such as "80% or more to 100% accuracy" or "50% or more to less than 80% accuracy". Thus, the screen or the like may be adjusted based on such a reference.

In addition, by having the subject appropriately create content subdividing the questionnaire method of the technique for defining and classifying the individual information and the items of the performance test table, and increasing the population, it is possible to raise the accuracy of the conversion information.

2. First Embodiment

Biomolecule Data on the Body Surface/Monoamine Types (1) Overview

The inventors focused on the "types and amounts of body surface biomolecules" and "activities in the daily lives of humans", and, as the result of intensive research regarding the relationship with "the individuality, temperament, and character of a subject", found that it is possible to create information relating to the individuality, temperament, and character of a subject measured from the amounts and quantity ratio changes of biomolecules on the skin in conjunction with activities in daily life.

Specifically, the monoamines on the body surface in each living activity were measured and individual information was obtained. More specifically, when dopamine and L-dopa, which are catecholamines, were measured, new findings were discovered that were completely unexpected. Hereafter, description will be given with respect to catecholamines; however, the present application is not limited thereto.

Here, typically, since it is possible to obtain various information about the physiological state and disease from the amounts of the respective catecholamine biomolecules, measurement of the catecholamine metabolites in blood and the catecholamine metabolites in urine is performed by the collection of blood and urine. However, in the past, accurate values were not measured because the amount of catecholamines changes as a result of psychological stress due to the blood and urine collection; however, according to the novel findings of an embodiment of the present application, it is possible to measure accurate values.

Figure 19:
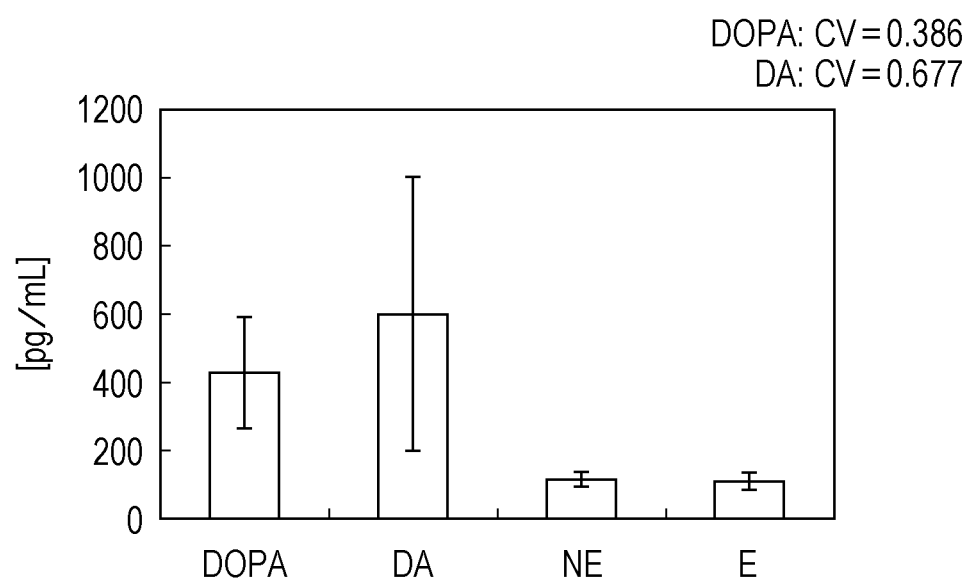
FIG. 19 is a diagram showing individual differences (width of the vertical line) between average values (bar graph) of each biomolecule amount of catecholamines on the skin in the embodiment of the present application. DOPA: L-dopa, DA: dopamine, NE: noradrenaline, E: adrenaline.

Specifically, as shown in FIG. 19, it was found that, among catecholamines (dopamine, L-dopa, noradrenaline, adrenaline) on the body surface, the biomolecules having large individual differences are dopamine, and that the other three biomolecules have small individual differences. In addition, since the detected amounts of dopamine and L-dopa on the body surface are great, it was considered that these are suitable for various kinds of analysis and determination. These findings had not yet been discovered.

Figure 20:
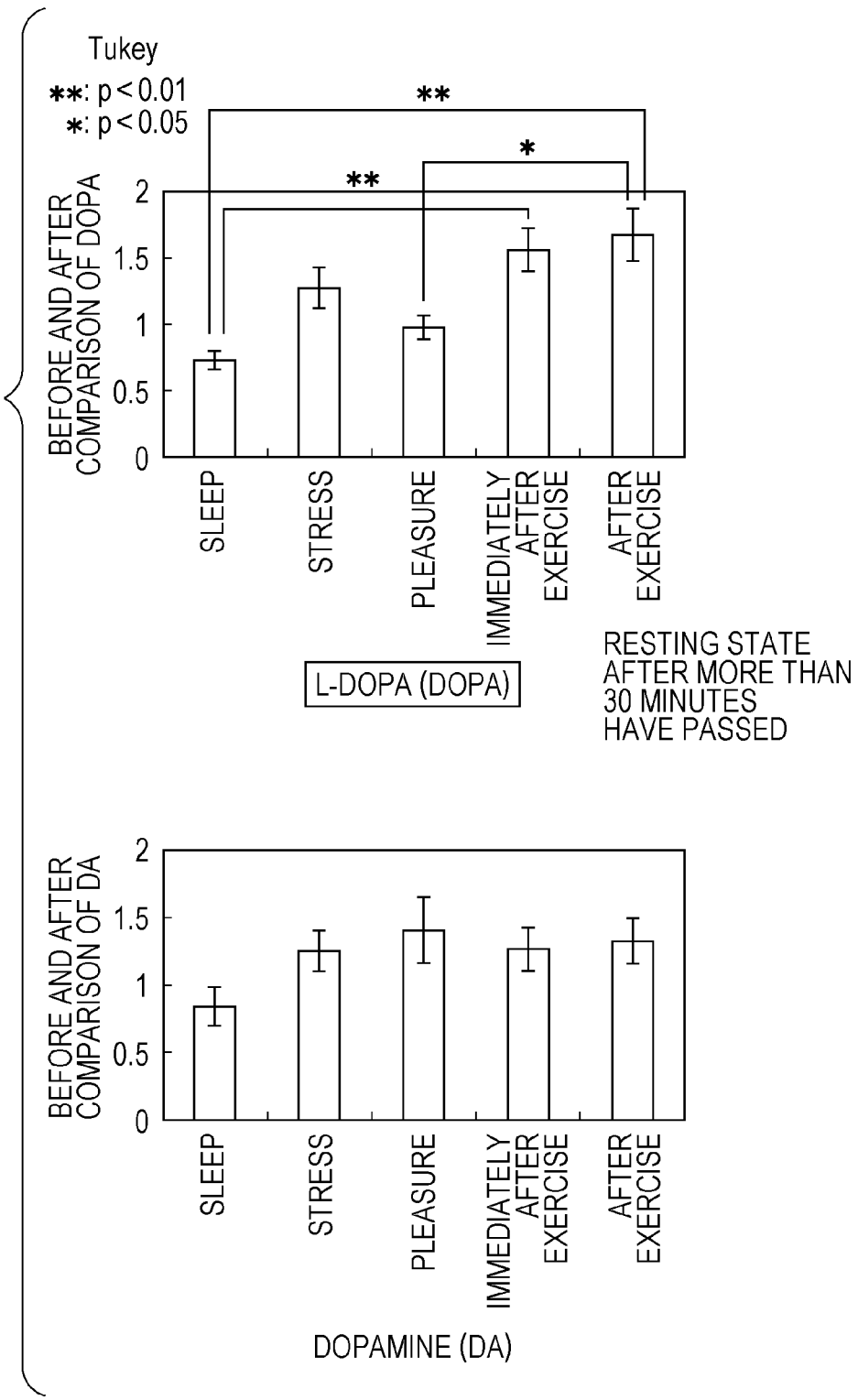
FIG. 20 is a diagram showing changes according to each load of the dopamine and L-dopa (sleep, stress, recreation, immediately after exercise, and a resting state after 30 minutes or more have passed after exercise) in another embodiment of the present application.

Further, as shown in FIG. 20, it is clear that the amount of L-dopa on the body surface has smaller individual differences and is suitable for the evaluation of changes due to various factors. On the other hand, it is clear that the amount of dopamine on the body surface has greater individual differences and is suitable for the evaluation of individual background amounts.

Figure 22:
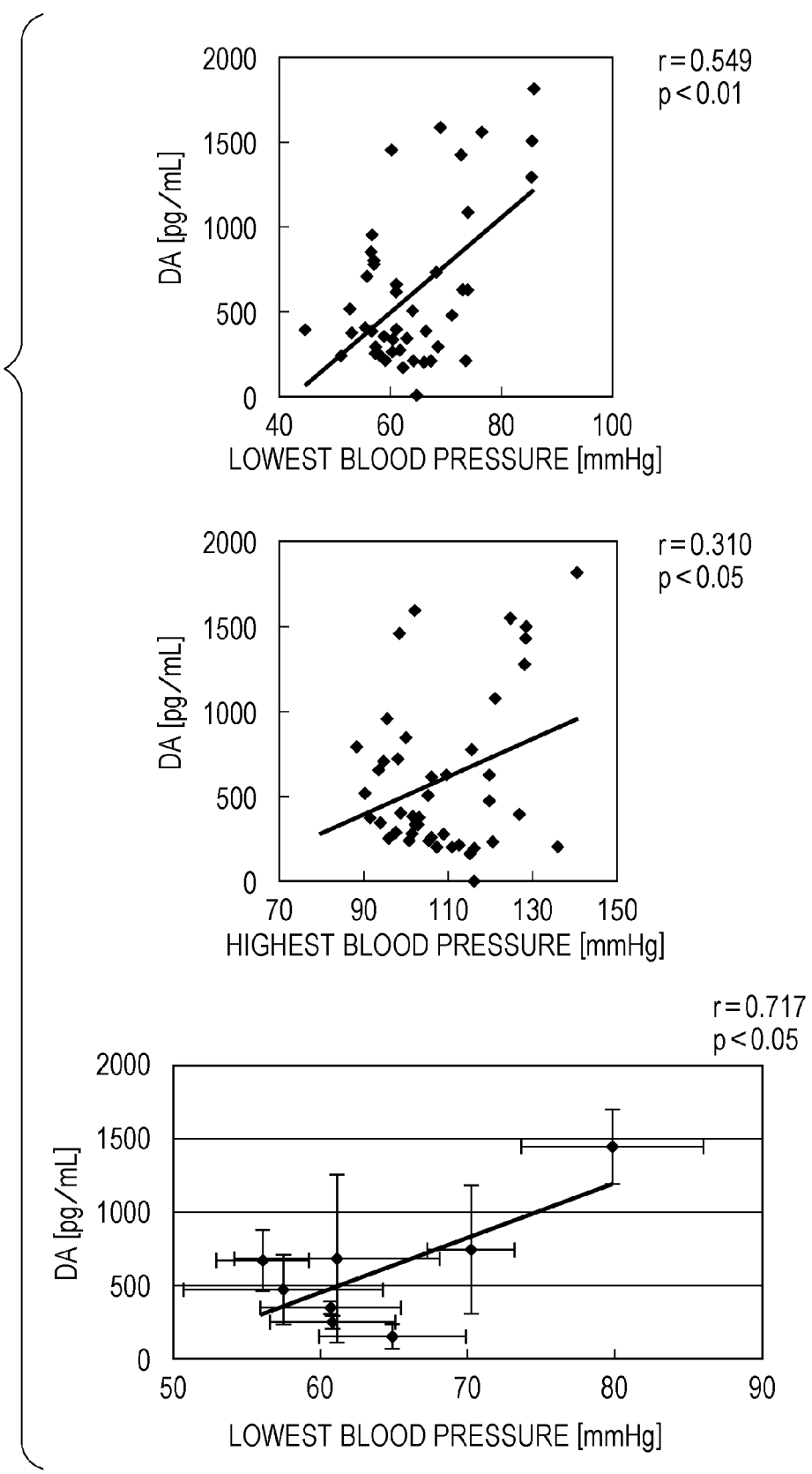
FIG. 22 is a diagram showing a correlation between dopamine on the skin and changes of psychological indicators (highest blood pressure and lowest blood pressure) (lowest blood pressure).

Further, as shown in FIG. 21, it is clear that the changes in the L-dopa on the body surface show a correlation with changes relating to the blood flow such as heart rate and blood pressure. Further, as shown in FIG. 22, it is clear that the amount of dopamine on the body surface correlates with diastolic blood pressure.

For this reason, in the present application, it is possible to estimate the changes of catecholamines according to external factors and internal factors using the change amounts of L-dopa among the catecholamines measured on the body surface. Thus, it was considered that it is possible to evaluate the external factors and internal factors affecting a subject and evaluate the temperament of the subject for measurement according to genetic factors and environmental factors using the dopamine amounts.

Here, in the findings, the details of living activity data are also acquired and the individual information is determined based on the results of studies of trial and error, and the catecholamine biomolecule data on the body surface.

Incidentally, catecholamines are a generic name for biogenic amines found mainly in the brain, the sympathetic nervous system, and the adrenal medulla, and representative examples thereof are dopamine, noradrenaline, and adrenaline. The catecholamines are biosynthesized in order of tyrosine, L-dopa, dopamine, noradrenaline, and adrenaline.

Catecholamines act as transmitters in the central or peripheral nerves and act as hormones of the adrenal medulla, and are understood to change significantly according to external influences and internal activities in everyday life.

As diseases relating to catecholamines, there are brown fat cell tumors in which the secretion of catecholamines due to abnormality of the adrenal medulla is increased, and, as central system abnormalities, there is Parkinson's disease in which the dopamine amount deteriorates as a result of the dopamine nerves breaking down. In addition, it is reported that abnormalities of dopamine are related to schizophrenia and ADHD, and there are findings that noradrenaline has a relationship with depression.

Dopamine primarily functions as a neurotransmitter in the central nervous system, and has effects such as improving the efficiency of recreation, desire, motivation, and learning relating to neural control of movement, adjustment of hormones, and the reward system. Dopamine also functions as a hormone secreted by the adrenal medulla and has an effect on the heart muscles, kidneys, and the vascular endothelium and it has also been found to influence blood pressure or heart rate.

Further, particularly, the central feature relating to dopamine is that, not just the changes, but the background amounts due to genetic factors and due to environmental factors are also important, and it is understood that there is a relationship between polymorphisms in genes relating to dopamine and temperament, learning ability and the like.

Noradrenaline primarily functions as a neurotransmitter secreted by the sympathetic nervous system, and, together with the action of hormones secreted by the adrenal medulla, is involved in the reaction of each organ to stimulation by the sympathetic nervous system, for example, a heart rate increase or metabolic changes. Noradrenaline is also understood to act as a central nervous system neurotransmitter.

Similarly to noradrenaline which has an effect as hormones of the adrenal medulla, adrenaline is understood to be involved in the reaction of each organ to stimulation by the sympathetic nervous system.

Serotonin has a function as a neurotransmitter in the central nervous system and a function as hormones produced from the small intestinal mucosa; as the central function, it is understood to be involved with circuits suppressing excitement, discomfort, and the like.

(2) Individual Information Determining Method Relating to the First Embodiment of the Present Application In the individual information determining method relating to the first embodiment of the present application, description will be given with parts overlapping with the above-described <1. Individual Information Determining Method> omitted.

The individual information determining method of the first embodiment preferably has the individual information analysis unit 1 and the body surface biomolecule data processing unit 2. Furthermore, it is also preferable to have the living activity data processing unit 3.

The first embodiment of the present application may perform individual information determination according to the above-described <1. Individual Information Determining Method>.

The body surface biomolecule data preferably relate to monoamines. Monoamine precursors and monoamine metabolites from monoamines are preferable. Further, catecholamines are preferable. As the catecholamines, L-dopa, dopamine, noradrenaline, adrenaline and the like may be exemplified. By using such biomolecules, as described above, it is possible to determine (create) individual information with higher accuracy.

In addition, among the biomolecule data of the monoamines, that of one or both of the dopamine and L-dopa is preferable. As the conversion information at this time, it is preferable to use the filings used in FIG. 5, FIGS. 7 to 18, FIG. 21, FIG. 22, and the like, and it is preferable that these be stored in the storage unit 104. In this manner, it is possible to easily determine (create) individual information with higher accuracy.

Further detailed description will be given below; however, this is illustrative only and the present application is not limited thereto.

From the biomolecule data (preferably the amount (for example, the amount of change)) of the dopamine on the body surface, the increase or decrease of dopamine for living activities such as sleep or exercise is determined. Alternatively, from the sleep data (preferably the quantity ratio for before and after) from the dopamine biomolecule data and the living activity data, the increase or decrease of the stress, recreation, or exercise of living activities is determined The above are preferably performed in accordance with conversion information such as "the dopamine average value and the L-dopa or dopamine (refer to FIG. 9)" and "dopamine during living activity (refer to FIG. 10)". Next, by using such conversion information to ascertain the data of one of these, there is an advantage in that it is possible to easily obtain the predicted data of the other.

Figure 9:
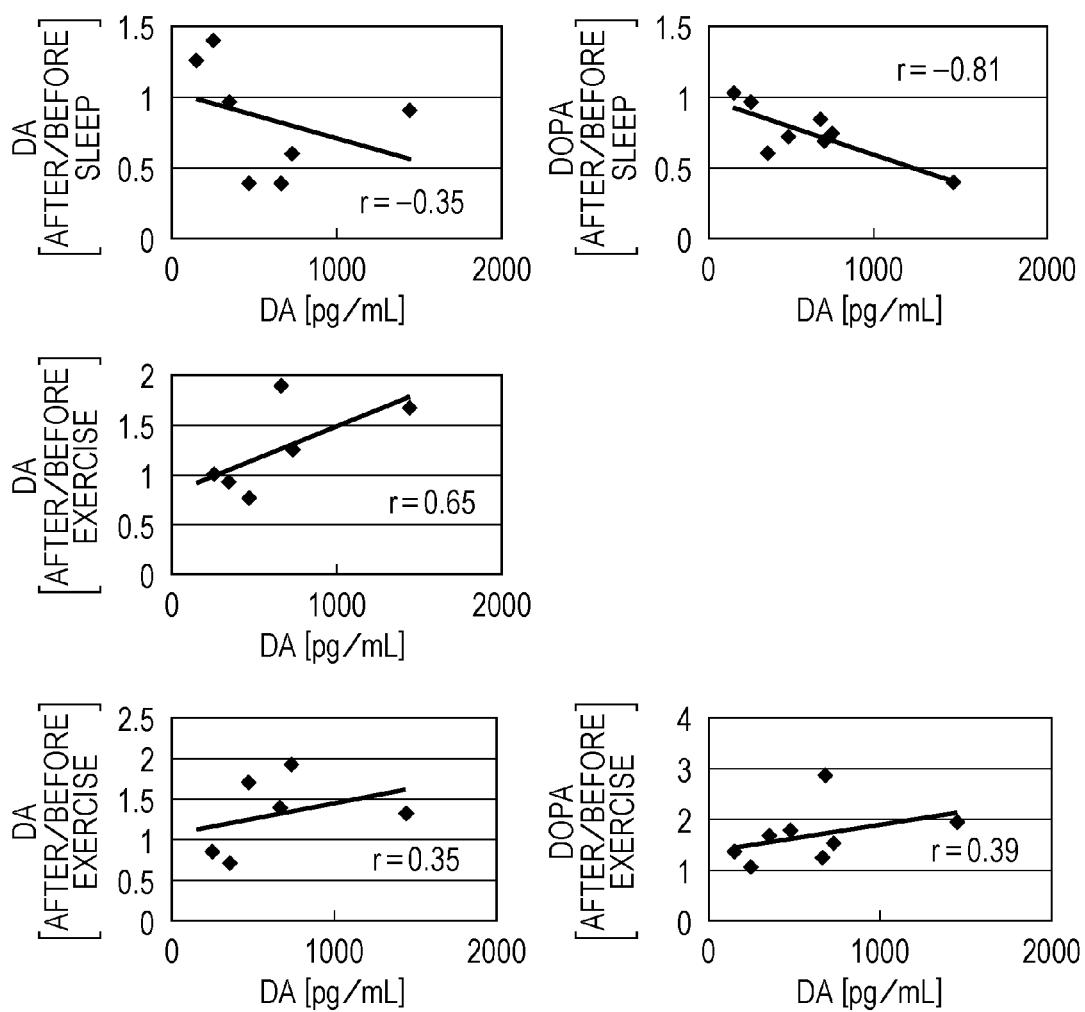
FIG. 9 is a diagram showing a correlation between dopamine average values and changes (dopa) in the embodiment of the present application.

In more detail, this is preferably performed based on the correlation (conversion information) between the dopamine average value (one day) and the dopamine and L-dopa of the living activities (refer to FIG. 9).

For example, in the dopamine (also called DA) and the L-dopa (also called L-DOPA) or dopamine of the living activities (refer to FIG. 9), DA [before and after sleep]: DA (negative), DA [before and immediately after exercise]: DA (positive), DA [before and after exercise]: DA (positive), L-DOPA [before and after sleep]: DA (negative), L-DOPA [before and after exercise]: DA (positive).

Figure 10:
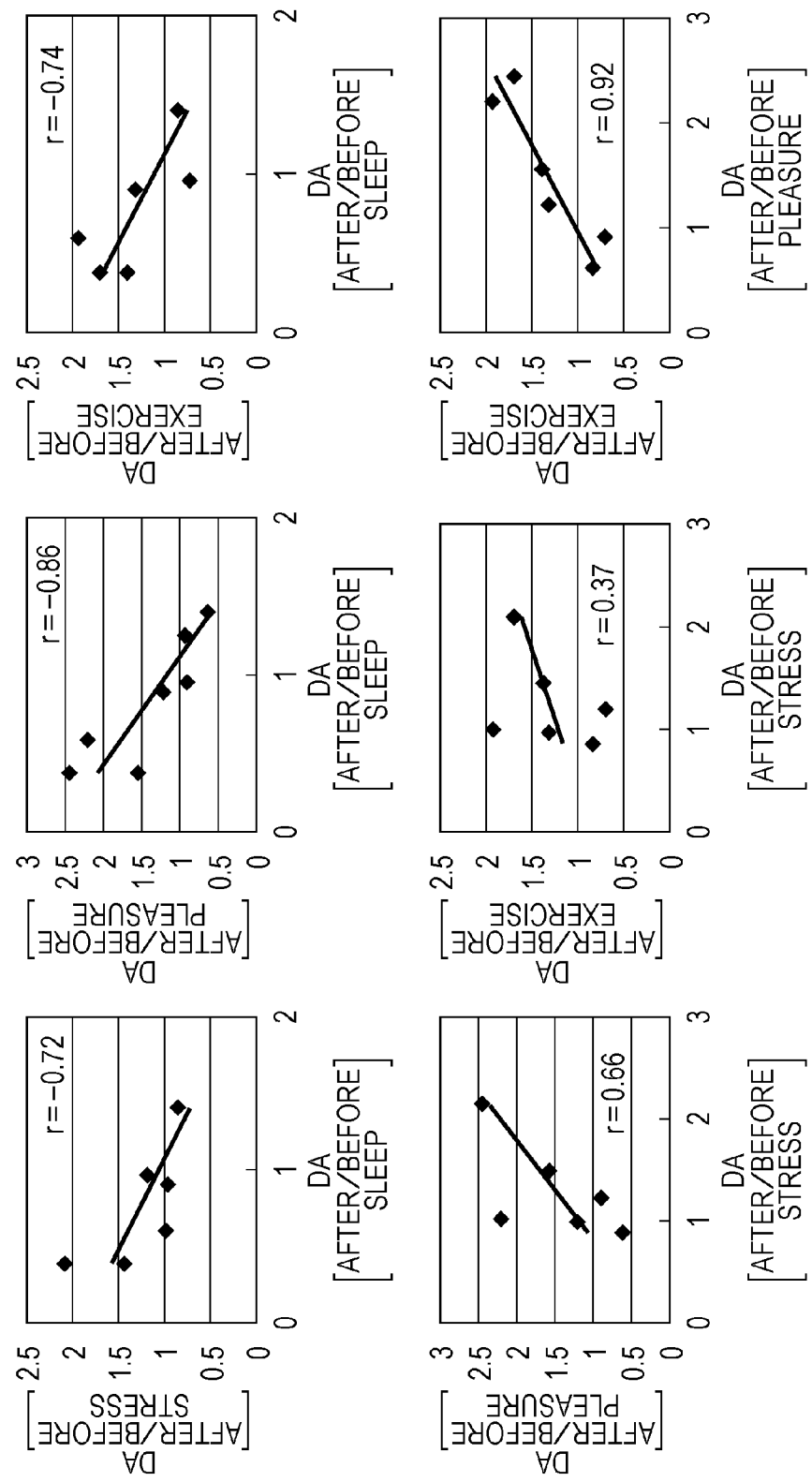
FIG. 10 is a diagram showing a correlation during dopamine changes in the embodiment of the present application.
Figure 11:
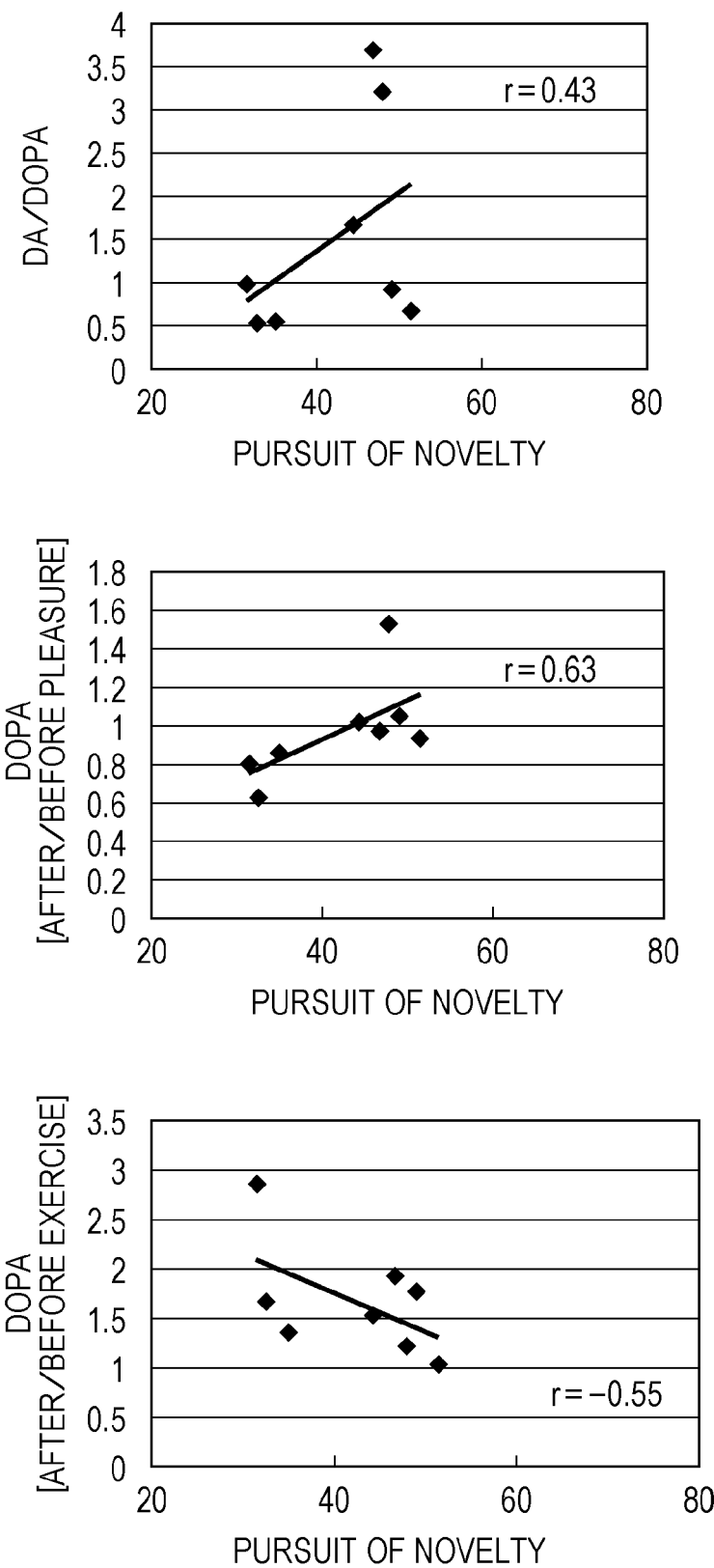
FIG. 11 is a diagram showing a pursuit of novelty correlation between character and dopamine (dopa) in the embodiment of the present application.

In addition, this is preferably performed based on the correlation (conversion information) between the dopamine amount of living activities and the other living activity dopamine amounts (refer to FIG. 10).

For example, in the dopamine during the living activities (refer to FIG. 10), DA [before and after stress]: DA [before and after sleep] (negative), DA [before and after recreation]: DA [before and after sleep] (negative), DA [before and after exercise]: DA [before and after sleep] (negative). Furthermore, DA [before and after recreation]: DA [before and after stress] (positive), DA [before and after exercise]: DA [before and after stress] (positive), DA [before and after exercise]: DA [before and after recreation] (positive).

In addition, for example, DA [before and after sleep] is the DA amount after sleep/the DA amount before sleep and the same applies to other "before and after" references.

From one or both of the dopamine biomolecule data on the body surface and the L-dopa biomolecule data on the body surface, temperament traits of pursuit of novelty, damage avoidance, compensation dependence, and persistent tendencies as well as character traits of self-orientation, cooperativeness, and self-transcendence are determined. In this manner, individual information of temperament and character may be obtained based on biomolecule data on the body surface (type, quantity ratio) and living activity data.

At this time, it is preferable that a single or a plurality of filings stored in the storage unit 104 or a filing transmitted from another unit be set as the conversion information, and that the individual information be determined (created) in accordance with such conversion information. In addition, when a plurality of filings (stock) is used, it is possible to search among these for more suitable filings. Here, there is an advantage in that it is possible to easily obtain the sought data when the suitable filing is applied to the acquired data.

As such a filing, for example, correlation data diagrams and the like as shown in the list of FIG. 5 and FIGS. 7 to 18, FIG. 21, and FIG. 22 may be exemplified.

Description will be given of the flow of individual information determination of an embodiment of the present application in [Step 1] to [Step 4] with reference to FIG. 3 and FIG. 5.

[Step 1]: The biomolecule data on the whole body surface from the body surface biomolecule collection unit 102 are transmitted to the body surface biomolecule data processing unit 2, where the specified substance and the amount thereof are calculated.

For example, the measurement results of the biomolecule apparatus on the body surface are transmitted from the body surface biomolecule collection unit 102 to the body surface biomolecule data processing unit 2, where the respective amounts of the dopamine and the L-dopa are calculated. The body surface biomolecule data are transmitted to the individual information analysis unit 1.

[Step 2]: Further, concurrently or separately with this, the living activity data from the living activity acquisition unit 103 are transmitted to the living activity data processing unit 3, where the data are classified with reference to the living conditions, period, and the like.

For example, the measurement results of acceleration sensors and the like are transmitted to the living activity data processing unit 3 from the living activity acquisition unit 103, where the data are specified as before exercise, during exercise, and after exercise. The living activity classification data are transmitted to the individual information analysis unit 1.

[Step 3]: Here, the body surface biomolecule data and the living activity data are separately or concurrently transmitted to the individual information analysis unit 1, where the body surface biomolecule data and the living activity data (living activity classification data) may be linked in parallel or classified.

For example, the "dopamine (amount)" and "L-dopa (amount)" of the transmitted body surface biomolecule data are linked with the "before exercise", "during exercise", and "after exercise" of the living activity classification data.

As an example, "amount"—"before exercise", "amount"—"during exercise", and "amount"—"after exercise" are classified under the heading of dopamine, and filed. Alternatively, filings are performed in a state of being linked in parallel with "dopamine", "amount thereof"—"before exercise", "during exercise", and "after exercise".

[Step 4]: Next, one or both of the "biomolecule data" and the "living activity data" in the "body surface biomolecule data and the living activity data at this time" are selected and conversion information is applied thereto.

Figure 13:
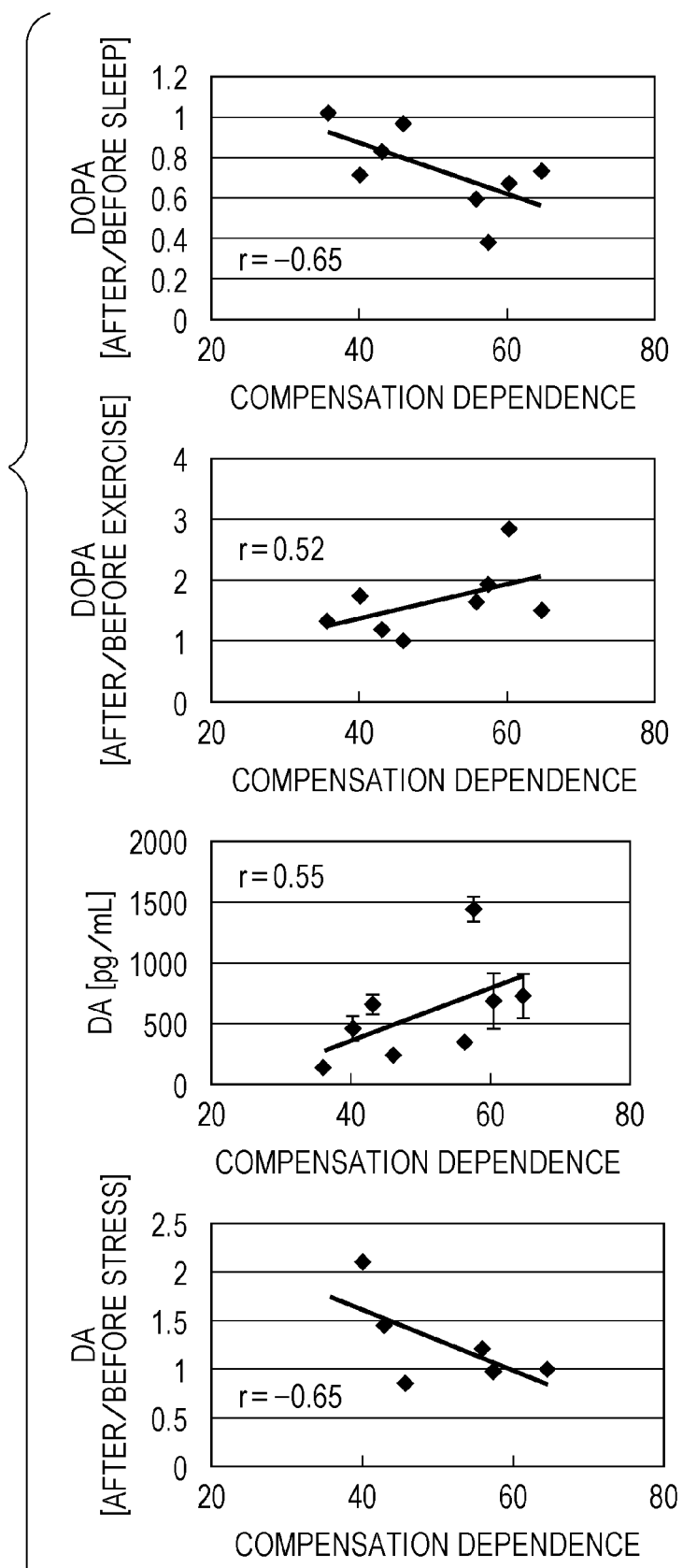
FIG. 13 is a diagram showing a compensation dependence correlation between character and dopamine (dopa) in the embodiment of the present application.

As an example, the conversion information of the DA list of FIG. 5 is applied to "dopamine amount"—"sleep" and it is determined that persistent tendencies are high and self-orientation is low. Further, with "before exercise", "dopamine amount"—"after exercise", the quantity ratio of the dopamine "after exercise/before exercise" is calculated, for example, when the quantity ratio equals one, the conversion information of the correlation diagram of compensation dependence of FIG. 13 is applied, and it is determined that the level of compensation dependence is 30%.

The determination results are output.

(3) Individual Information Determining Method Based on One or Both of Dopamine Biomolecule Data and L-Dopa and Living Activity Data Further, the following (A) to (E) are preferably as described in detail below; however, these are not limiting.

(A) Temperament of persistent tendencies as well as character traits of compensation dependence and cooperativeness are determined based on the average values of the biomolecules from the dopamine biomolecule data on the surface of the body surface and the living activity data. In this manner, it is possible to obtain individual information about temperament and character.

For example, in the dopamine average values (refer to FIG. 7), dopamine average value: compensation dependence (positive), DA average value: cooperativeness (positive), DA average value: persistent tendencies (negative).

(B) Temperament of pursuit of novelty and persistent tendencies is determined based on the biomolecule data of the ratio of (dopamine on the surface of the body surface/L-dopa on the surface of the body surface) from the biomolecule data on the surface of the body surface and the average values of the biomolecules from the living activity data. In this manner, it is possible to obtain individual information about temperament.

For example, in the DA average values/L-dopa average values (refer to FIG. 8), DA average value/L-DOPA average value: pursuit of novelty (positive), DA average value/L-DOPA average value: persistent tendencies (negative).

(C) It is preferable to determine the following (a) to (d) from the dopamine biomolecule data on the surface of the body surface and the living activity data.

(a) Based on sleep data, temperament traits of persistent tendencies and character traits of self-orientation.

(b) Based on stress data, temperament traits of compensation dependence as well as character traits of self-orientation, cooperativeness and self-transcendence.

(c) Based on recreation data, temperament traits of persistent tendencies as well as character traits of self-orientation, cooperativeness, and self-transcendence.

(d) Based on exercise data, temperament traits of damage avoidance, and persistent tendencies as well as character traits of self-orientation, cooperativeness, and self-transcendence.

In this case, the body surface biomolecule data on the body surface and the living activity data at this time are selected. The DA table is selected from the filings (list) shown in FIG. 5. At this time, the living activity data at the time of biomolecule collection are determined to be any one of (a) sleep data, (b) stress data, (c) recreation data, and (d) exercise data. Individual information with a high correlation relationship is determined and the ratio thereof is also determined as appropriate. Based on this, individual information is created and output.

Figure 14:
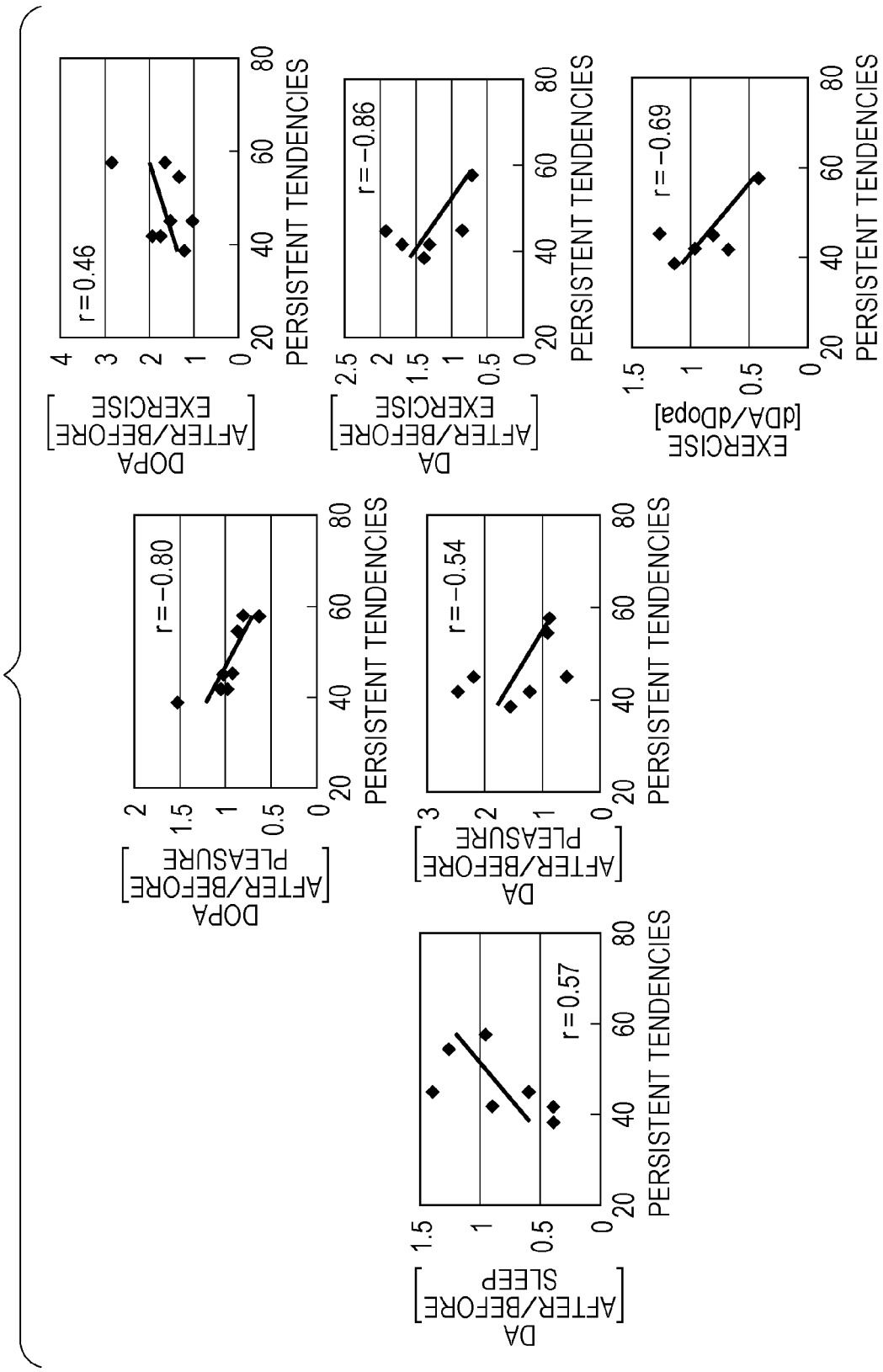
FIG. 14 is a diagram showing a persistent tendencies correlation between character and dopamine (dopa) in the embodiment of the present application.

For example, when the DA [before and after sleep] is "one", it is determined from the DA [before and after sleep] of FIG. 14 to show persistent tendencies 50%.

(D) It is preferable that the following (a) to (d) be determined from the body surface L-dopa biomolecule data on the surface and the living activity data.

(a) Based on sleep data, temperament traits of compensation dependence and character traits of cooperativeness.

(b) Based on stress data, temperament traits of damage avoidance as well as character traits of self-orientation and cooperativeness.

(c) Based on recreation data, temperament traits of pursuit of novelty and persistent tendencies as well as character traits of self-orientation and cooperativeness.

(d) Based on exercise data, temperament traits of pursuit of novelty, compensation dependence and persistent tendencies as well as character traits of cooperativeness and self-transcendence.

This determination may be performed according to the above-described "dopamine biomolecule data". For example, when the DOPA [before and after sleep] is "one", it is determined from the DOPA [before and after sleep] of FIG. 13 to show compensation dependence 30%.

(E) It is preferable that the following (a) to (d) be determined from the biomolecule data of the ratio (dopamine on the surface of the body surface/L-dopa on the surface of the body surface) from the body surface biomolecule data on the surface and the living activity data.

(a) Based on sleep data, temperament traits of persistent tendencies and character traits of self-orientation.

(b) Based on stress data, temperament traits of damage avoidance as well as character traits of self-orientation, cooperativeness and self-transcendence.

(c) Based on recreation data, character traits of self-orientation, cooperativeness, and self-transcendence.

(d) Based on exercise data, temperament traits of pursuit of novelty, damage avoidance and persistent tendencies.

This determination may be performed according to the above-described "dopamine biomolecule data". For example, when recreation [DA/L-DOPA] is "one", it is determined from the recreation [dDA/dDopa] of FIG. 16 to show self-orientation 60%.

3. Second Embodiment

Biomolecule Data on the Body Surface/Steroid Hormone Types (1) Overview

The inventors focused on the "types and amounts of body surface biomolecules" and carried out intensive research on the relationship with "the individuality, temperament, and character of a subject". As a result, it was found that there is a correlation between the amount of steroid hormones on the body surface and influence on risk-taking behavior, fairness, aggressive and dominant tendencies and trust, and competition and motivation in teams.

Here, as steroid hormones, for example, cortisols, androgens, and estrogens may be exemplified. These are secreted from the adrenal cortex, the ovaries and testes, and the like. Androgens and estrogens are called sex hormones, and it is said that the amounts thereof and the balance in the body is important. Thus, typically, steroid hormones were measured by blood collection, which was not practical since the psychological burden was large.

Further, unexpectedly, the present inventors clarified a way to better determine the "individuality, temperament, and character of a subject" by measuring the steroid hormones on the body surface even without directly collecting blood.

(2) Individual Information Determining Method Relating to the Second Embodiment of the Present Application In the individual information determining method relating to the second embodiment of the present application, description will be omitted regarding points overlapping with the above-described <1. Individual Information Determining Method>.

The individual information determining method relating to the second embodiment of the present application preferably has the individual information analysis unit 1 and the body surface biomolecule data processing unit 2. Furthermore, the method preferably has the living activity data processing unit 3.

The second embodiment of the present application may perform individual information determination according to the above-described <1. Individual Information Determining Method>.

The body surface biomolecule data on the surface is preferably steroid hormones. Types of testosterone are more preferable. By using these biomolecules, it is possible to determine (create) individual information with higher accuracy as described above.

In addition, testosterone biomolecule data is preferable in the steroid hormones biomolecule data. As the conversion information at this time, it is preferable to use the filings of FIG. 26, Table 2 and the like, and it is preferable that these be stored in the storage unit 104. In this manner, it is possible to easily determine (create) individual information with higher accuracy as described above.

Further detailed description will be given below; however, this is illustrative only and the present application is not limited thereto.

From the biomolecule data (preferably the amount (for example, the amount of change)) of testosterone on the surface of the body surface, determination is made regarding the influence on risk-taking behavior, fairness, aggressive and dominant tendencies and trust, and competition and motivation in teams.

For example, regarding risk-taking behavior, determination is preferably performed in accordance with conversion information such as "testosterone concentration on the skin and risk-taking ratio (refer to FIG. 26 and Table 2)".

The risk-taking ratio is determined from the testosterone biomolecule data on the surface of the body surface. In this manner, it is possible to obtain individual information of temperament and character based on biomolecule data (type, amount) on the surface of the body surface.

At this time, a single or a plurality of filings stored in the storage unit 104 or the filings transmitted from other units are set as the conversion information, and the individual information is preferably determined (created) according to this conversion information. In addition, when a plurality of filings (stock) is used, it is possible to search among these for more suitable filings. Here, there is an advantage in that it is possible to easily obtain the sought data when the suitable filing is applied to the acquired data.

As such a filing, for example, correlation data diagrams and the like as shown in FIG. 26 and Table 2 may be exemplified.

Figure 4:
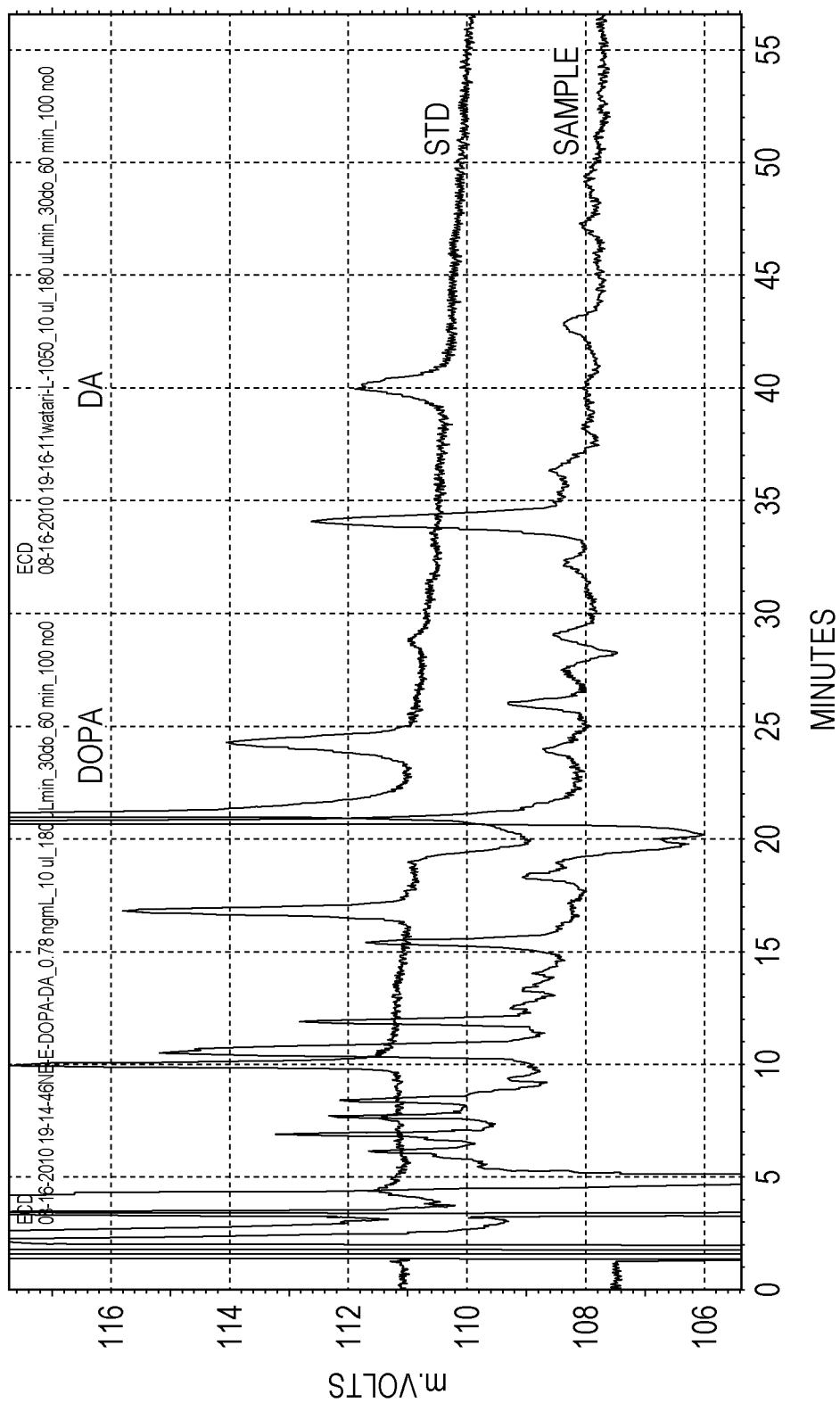
FIG. 4 is a diagram showing the results measured by HPLC of biomolecules collected from on the surface of the body surface (biomolecule data on body surface). DA: dopamine, DOPA: L-dopa, STD: reference standard, Sample: collection sample.

The individual information determining flow of an embodiment of the present application will be described using [Step 1] to [Step 3] with reference to FIGS. 3 and 4.

[Step 1]: The measurement results of the biomolecules on the body surface of the body surface biomolecule collection unit 102 are transmitted to the body surface biomolecule data processing unit 2, and become body surface biomolecule data (specification of the substance (identification) and the amount thereof).

At this time, such data may be stored in the storage unit 104.

[Step 2]: Next, in the individual information analysis unit 1, conversion information (for example, a conversion formula, a conversion table, or the like) corresponding to the "body surface biomolecule data" is selected from a conversion information file (data).

[Step 3]: Then, individual information (specifically, temperament, character, individuality, and the like) having a correlation to the "body surface biomolecule data" in the selected conversion information (for example, the case of correlation data) is selected based on the "biomolecule data", and determined as individual information. Further, the degree of tendencies of temperament, character, and the like is determined as a ratio (%). The determination results are displayed.

4. Individual Information Determining Device

Description will be given regarding the individual information determining device according to an embodiment of the present application. The individual information determining device is not particularly limited as long as it has a configuration which may realize the above-described individual information determining method.

Below, description will be given of an example of a preferable embodiment.

FIG. 3 is a block diagram (schematic diagram) showing the configuration of an individual information determining device according to an embodiment of the present application.

The individual information determining device 10 is provided with biomolecule data processing unit 2 processing biomolecules on a surface of the body surface, a living activity data processing unit 3, and an individual information analysis unit 1.

When one or both of biomolecules on the surface of the body surface (below, "body surface biomolecules") data processing function and a living activity data processing function are performed in the individual information analysis unit 1, one or both of the body surface biomolecule data processing unit 2 and the living activity data processing unit 3 may not be provided.

(1) Biomolecule Data Processing Unit on the Body Surface

The biomolecule data processing unit on the body surface 2 is realized, for example, by a CPU, a ROM, a RAM, or the like. In addition, the body surface living data processing function may be performed by the individual information analysis unit 1.

(2) Living Activity Data Processing Unit

The living activity data processing unit 3 is realized, for example, by a CPU, a ROM, a RAM, or the like. In addition, the body surface living data processing function may be performed by the individual information analysis unit 1.

(3) Individual Information Analysis Unit

The individual information analysis unit 1 is realized, for example, by a CPU, a ROM, a RAM, or the like.

The individual information analysis unit 1 controls the biomolecule data processing unit 2 and the living activity data processing unit 3.

The individual information analysis unit 1 creates individual information according to conversion information based on the body surface biomolecule data obtained from the biomolecule data processing unit 2 and living activity data obtained from the living activity data processing unit 3.

As an example, as individual information, temperament traits of pursuit of novelty, damage avoidance, and persistent tendencies, as well as character traits of self-orientation, cooperativeness, and self-transcendence may be exemplified. Moreover, as individual information, temperament and character traits of risk-taking behavior, fairness, aggressive and dominant tendencies and trust, and competition and motivation in teams may be exemplified.

At this time, from among these, determination is performed and the individual information is created in accordance with the stored conversion information based on one or both of the body surface biomolecule data and the living activity data.

(4) Storage Unit

Further, a storage unit 104 may also be provided. The storage unit 104 may be removable. At this time, the individual information analysis unit 1 may also control the storage unit 104. Then, the storage unit 104 may store the biomolecule data, the living activity data, and the conversion information. Further, the storage unit 104 may transmit and receive these data to and from the individual information analysis unit 1 in a wired or wireless manner.

(5) Output Unit

Further, an output unit 105 may also be provided. The output unit 105 may be removable. At this time, the individual information analysis unit 1 may also control the output unit 105. Then, the output unit 105 outputs the determination of individual information created by the individual information analysis unit 1. This output may be a screen display, audio output, or the like.

(6) Electronic Apparatus

It is preferable that the individual information determining unit of an embodiment of the present application be provided in an electronic apparatus. Further, the program of an embodiment of the present application and the information recording medium in which the program is stored may be provided or installed in the electronic apparatus.

Using the individual information determining method of an embodiment of the present application (temperament, character information), it is possible to optimize the effects and operation of various devices, software, and the like. As electronic apparatuses that may be optimized, for example, exercise equipment, sleep-related devices, entertainment devices (software), educational equipment (software), equipment with an operation causing a stress burden (software) and the like may be exemplified.

In addition, by using an embodiment of the present application, it is possible to provide and recommend products, information, and the like matching an individual's temperament and character.

Further, in the case of recreational devices (such as gaming devices), by applying an embodiment of the present application to the recreational devices, it is also possible to play customized games according to the temperament or character of an individual. For example, in the case of the pursuit of novelty, in order to avoid aggression, and in the case of damage avoidance, in order to avoid a feeling of fatigue, lowering the brightness of a screen or the like may be exemplified. Alternatively, in internet communication through social networks or the like, it is possible to facilitate communication by showing the present character of a user.

Furthermore, according to an embodiment of the present application, by giving a measurement of temperament and character with respect to mental illness such as schizophrenia, ADHD and depression and developmental disabilities, it is possible to assist with diagnosis and treatment thereof. Further, by giving a measurement of temperament and character with respect to neurodegenerative diseases associated with personality disorders such as Alzheimer's disease, Parkinson's disease, and the like, it is possible to assist with diagnosis and treatment thereof.

In addition, according to an embodiment of the present application, it is possible to determine the type and amount of biomolecules from the body surface biomolecules and evaluate the likelihood of risk-taking behavior. In particular, since it is possible to easily and non-invasively measure the risk-taking tendency of a user at this time, it is possible to measure aptitude for daily work and professional duties.

For example, it is possible to evaluate the aptitude for gambling or for high powered professional duties such as trading. In particular, there is an advantage in that it is possible to make a short-term determination such as selecting a promising trader on a particular day.

In addition, according to an embodiment of the present application, since it is possible to easily measure the body surface biomolecules on the surface and to easily determine the type of the biomolecules, it is also possible to measure the tendency to be aggressive and dominant, the tendency to take risk, the compensation dependence tendency, the tendency to trust others, aptitude for team activities, motivation for professional duties and the like.

Since these tendencies change daily even in the same person, daily measurement is performed together with the recording of various events, and it is considered that an embodiment of the present application may also be applied to self-management, team management, and the like. In addition, using these values, it is possible to use an embodiment of the present application as an entertainment tool, communication tool, or the like for assessing affinity with other people.

5. Hardware Configuration of Embodiments of the Present Application

Figure 25:
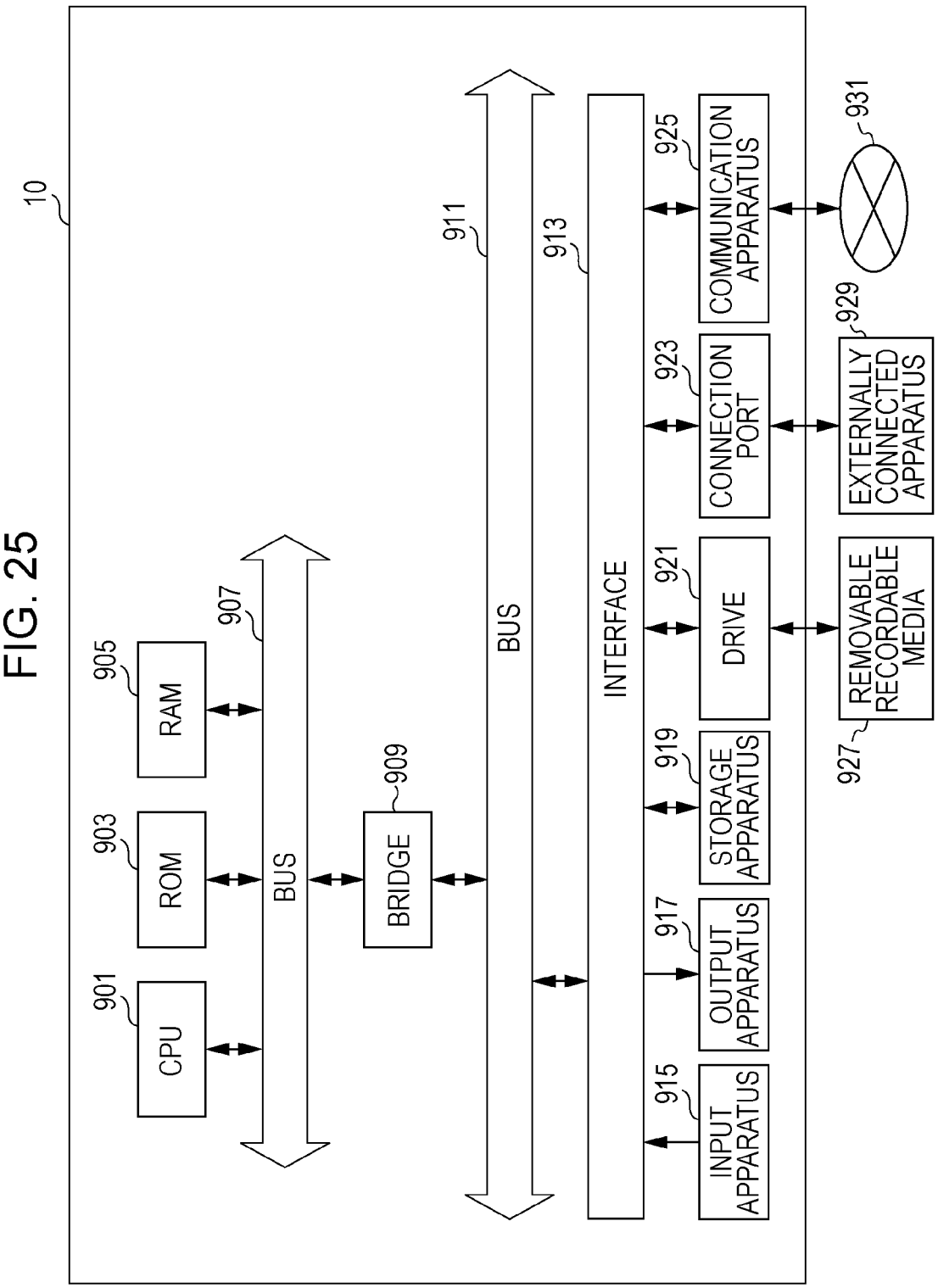
FIG. 25 is a block diagram for describing a hardware configuration of the individual information determining device according to the embodiments of the present application.

Referring to FIG. 25, detailed description will be given regarding the hardware configuration of the individual information determining device 10 according to an embodiment of the present application. FIG. 25 is a block diagram for describing the hardware configuration of the individual information determining unit 10 according to an embodiment of the present application.

The individual information determining device 10 is provided with a CPU 901, a ROM 903, and a RAM 905 in addition to the individual information analysis unit 1. Further, the individual information determining device 10 is also provided with a host bus 907, a bridge 909, an external bus 911, an interface 913, the input device 915, an output device 917, a storage device 919, a drive 921, a connection port 923, and a communication device 925.

The CPU 901 functions as a calculation processing apparatus and control apparatus, and controls the entirety or a part of the operation inside the individual information determining device 10 according to each type of program recorded in the ROM 903, the RAM 905, the storage device 919, or the removable recording medium 927. The ROM 903 stores programs, calculation parameters and the like used by the CPU 901. The RAM 905 primarily stores programs used in the performance of the CPU 901 and parameters and the like to be appropriately changed in the performance. These are interconnected by a host bus 907 configured by an internal bus such as a CPU bus.

The host bus 907 is connected to the external bus 911 such as a PCI (Peripheral Component Interconnect/Interface) bus through the bridge 909.

The input device 915, for example, is an operation unit for the user to perform operations such as a mouse, a keyboard, a touch panel, buttons, switches, levers, or the like. In addition, for example, the input device 915 may be a remote control unit (commonly called a remote control) using infrared rays or other radio waves, or may be an external connection device (compact terminal) 929 such as a mobile phone or a PAD linked to the operation of the individual information determining device 10. In addition, for example, the input device 915 is configured by an input control circuit or the like producing an input signal and performing output thereof to the CPU 901 based on information input by the user using the above-described operation unit. The user of the individual information determining device 10 may input various types of data and instruct processing operations with respect to the individual information determining device 10 by operating the input apparatus 915.

The output device 917 is configured by an apparatus capable of visually or visually and audibly notifying a user of acquired information. As such a device, there are a CRT display device, a liquid crystal display device, a plasma display device, an EL display device, a display device such as a lamp or the like, an audio output device such as speakers and headphones, a printer device, a mobile phone, a fax machine and the like. The output device 917, for example, outputs results obtained by various processes performed by the individual information determining device 10. Specifically, the display device displays the results obtained by the various processes performed by the individual information determining device 10 as text or images. On the other hand, the audio output device converts the audio signal made of reproduced audio data, acoustic data, or the like into an analog signal and performs output thereof.

The storage device 919 is a device for storing data configured as part of the storage unit of the individual information determining device 10. The storage device 919 may be configured from, for example, a magnetic storage device such as an HDD (Hard Disk Drive), a semiconductor storage device, an optical storage device, a magneto-optical storage device, or the like. The storage unit 919 stores programs and various types of data executed by the CPU 901, and various types of data acquired externally.

The drive 921 is a reader/writer for the storage medium, and may be incorporated within the individual information determining device 10 or without. The drive 921 reads out information recorded in the removable recording medium 927 such as a mounted magnetic disk, an optical disc, a magneto-optical disc, a semiconductor memory, or the like, and performs output thereof to the RAM 905. Further, the drive 921 is capable of writing to record on the removable recording medium 927 such as the mounted magnetic disk, the optical disc, the magneto-optical disc, the semiconductor memory, or the like.

The removable recording medium 927 is, for example, DVD media, HD-DVD media, or the like. Further, the removable recording medium 927 may be an SD Memory Card (Secure Digital memory card) or the like. In addition, the removable recording medium 927 may be, for example, an IC card (Integrated Circuit card) mounted with a contactless IC chip or an electronic apparatus or the like.

The connection port 923 is a port for directly connecting to a device and the individual information determining unit 10. As an example of the connection port 923, there are a USB (Universal Serial Bus) port, an IEE1394 port such as i.Link, an SCSI (Small Computer System Interface) port and the like. As other examples of the connection port 923, there are an RS-232C port, optical audio terminal, an HDMI (High-Definition Multimedia Interface) port and the like. By connecting an external connection device 929 to the connection port 923, the individual information determining device 10 may acquire various types of data directly from the external connection device 929, or provide various types of data to the external connection device 929.

The communication device 925 is a communication interface configured by a communication device for connecting to a communication network 931, for example. The communication device 925, for example, is a wired or wireless LAN (Local Area Network), a communication card for WUSB (Wireless USB) use, or the like. In addition, the communication device 925 may be a router for optical communication, a router for ADSL (Asymmetric Digital Subscriber Line) use, or a modem or the like for use in various types of communication.

The communication device 925, for example, may transmit and receive signals or the like based on predetermined protocols such as TCP/IP or the like, for example. In addition, the communication network 931 connected to the communication device 925 is configured by a network or the like connected in a wired or wireless manner, and may use, for example, the Internet, a LAN for home use, infrared communication, radio wave communication, satellite communication, or the like.

Here, an embodiment of the present application may adopt the following configurations.

[1] An individual information determining method determining individual information of a subject based on one or a plurality of pieces of biomolecule data collected from a surface of a body surface of the subject.

[2] The individual information determining method according to [1], in which individual information of the subject is determined based on one or a plurality of pieces of biomolecule data collected from the surface of the body surface of the subject and living activity data at the time of collection.

[3] The individual information determining method according to [1] or [2], in which the living activity data are living activity classification data.

[4] The individual information determining method according to any one of [1] to [3], in which the biomolecule data on the surface of the body surface are data quantifying monoamines or steroid hormones.

[5] The individual information determining method according to [4], in which the biomolecule data of the monoamines are one or both of dopamine and L-dopa biomolecule data.

[6] The individual information determining method according to [5], which determines a dopamine increase or decrease in living activities of sleep or exercise from dopamine biomolecule data on the surface of the body surface, or which determines an increase or decrease in living activities of stress, recreation, or exercise from sleep data from the dopamine biomolecule data and living activity data.

[7] The individual information determining method according to [5] or [6], in which temperament traits of pursuit of novelty, damage avoidance, compensation dependence, and persistent tendencies as well as character traits of self-orientation, cooperativeness, and self-transcendence are determined from one or both of the dopamine biomolecule data on the surface of the body surface and the L-dopa biomolecule data on the surface of the body surface.

[8] The individual information determining method according to any one of [5] to [7], which determines temperament traits of persistent tendencies as well as character traits of compensation dependence and cooperativeness based on average values of the biomolecules from the dopamine biomolecule data on the surface of the body surface and the living activity data.

[9] The individual information determining method according to any one of [5] to [7], which determines temperament traits of pursuit of novelty and persistent tendencies based on average values of the biomolecules from the biomolecule data of the ratio (dopamine on the surface of the body surface/L-dopa on the surface of the body surface) from the body surface biomolecule data on the surface and the living activity data.

[10] The individual information determining method according to any one of [5] to [7], which determines (a) temperament traits of persistent tendencies and character traits of self-orientation based on sleep data, (b) temperament traits of compensation dependence as well as character traits of self-orientation, and self-transcendence based on stress data, (c) temperament traits of persistent tendencies as well as character traits of self-orientation, cooperativeness, and self-transcendence based on recreation data, and (d) temperament traits of damage avoidance and persistent tendencies as well as character traits of self-orientation, cooperativeness, and self-transcendence based on exercise data, from the dopamine biomolecule data of a surface of the body surface and the living activity data.

[11] The individual information determining method according to any one of [5] to [7], which determines (a) temperament traits of compensation dependence as well as character traits of cooperativeness based on sleep data, (b) temperament traits of damage avoidance as well as character traits of self-orientation and cooperativeness based on stress data, (c) temperament traits of pursuit of novelty and persistent tendencies as well as character traits of self-orientation and cooperativeness based on recreation data, and (d) temperament traits of pursuit of novelty, compensation dependence and persistent tendencies as well as character traits of cooperativeness and self-transcendence based on exercise data, from the L-dopa biomolecule data of a surface of the body surface and the living activity data.

[12] The individual information determining method according to any one of [5] to [7], which determines (a) temperament traits of persistent tendencies as well as character traits of self-orientation based on sleep data, (b) temperament traits of damage avoidance as well as character traits of self-orientation, cooperativeness, and self-transcendence based on stress data, (c) character traits of self-orientation, cooperativeness, and self-transcendence based on recreation data, and (d) temperament traits of pursuit of novelty, damage avoidance, and persistent tendencies based on exercise data, from the biomolecule data of the ratio (dopamine on the surface of the body surface/L-dopa on the surface of the body surface) from the body surface biomolecule data on the surface and the living activity data.

[13] The individual information determining method according to [4], which determines a tendency to be aggressive and dominant in living activities, a tendency to take risks, a compensation dependence tendency, and a tendency not to trust others from the testosterone biomolecule data on the surface of the body surface.

[14] An individual information determining device including an analysis unit creating individual information of a subject based on one or a plurality of pieces of biomolecule data collected from a surface of a body surface and living activity data at the time of collection.

[15] The individual information determining device according to [14], further including a biomolecule collection unit on the surface of the body surface collecting the biomolecule data on the surface of the body surface with minimal invasiveness, and an output unit outputting the individual information.

[16] The individual information determining device according to [15] or [16], further including a storage unit transmitting and receiving the biomolecule data on the surface of a body surface and the living activity data to and from the analysis unit and performing storage thereof.

In the individual information determining device, the biomolecule data on the surface of the body surface and the living activity data are preferably those according to any one of [3] to [13] above.

It is preferable that the individual information determining device be provided with a program for realizing the individual information determining method according to any one of [1] to [13].

[17] An electronic apparatus including an analysis unit creating individual information of a subject based on one or a plurality of pieces of biomolecule data collected from a surface of a body surface and living activity data at the time of collection.

[18] The electronic apparatus according to [17] including an individual information determining device, an exercise device, a sleep-related device, a recreational device, an educational device, or an apparatus in which an operation causing a stress load takes place.

It is preferable that the electronic apparatus be provided with a program for realizing the individual information determining method according to any one of [1] to [13].

[19] A program causing a computer to execute: a biomolecule data processing function that processes biomolecules collected by a biomolecule collection unit on the surface of the body surface as biomolecule data on the surface of the body surface; a living activity data processing function that processes living activities at the time of collection acquired from a living activity acquisition unit as living activity data; and an analyzing function that determines temperament traits of pursuit of novelty, damage avoidance, and persistent tendencies as well as character traits of self-orientation, cooperativeness, and self-transcendence based on the biomolecule data on the surface of the body surface and the living activity data, and that creates individual information.

A program which realizes the individual information determining method according to [1] to [13] is preferable.

It is preferable that the individual information determining device or the electronic apparatus be provided with the program.

The above shows an example of a hardware configuration capable of realizing the functions of the individual information determining device 10 according to an embodiment of the present application. The respective constitutional components above may be configured using generic parts. Therefore, it is possible to appropriately change the hardware configuration to be used according to the level of technology at the time of implementing the present embodiment.

EXAMPLES

Examples are shown below in order to describe embodiments of the present application in more detail; however, embodiments of the present application are not limited thereto.

Example 1

Monoamines

Figure 23:
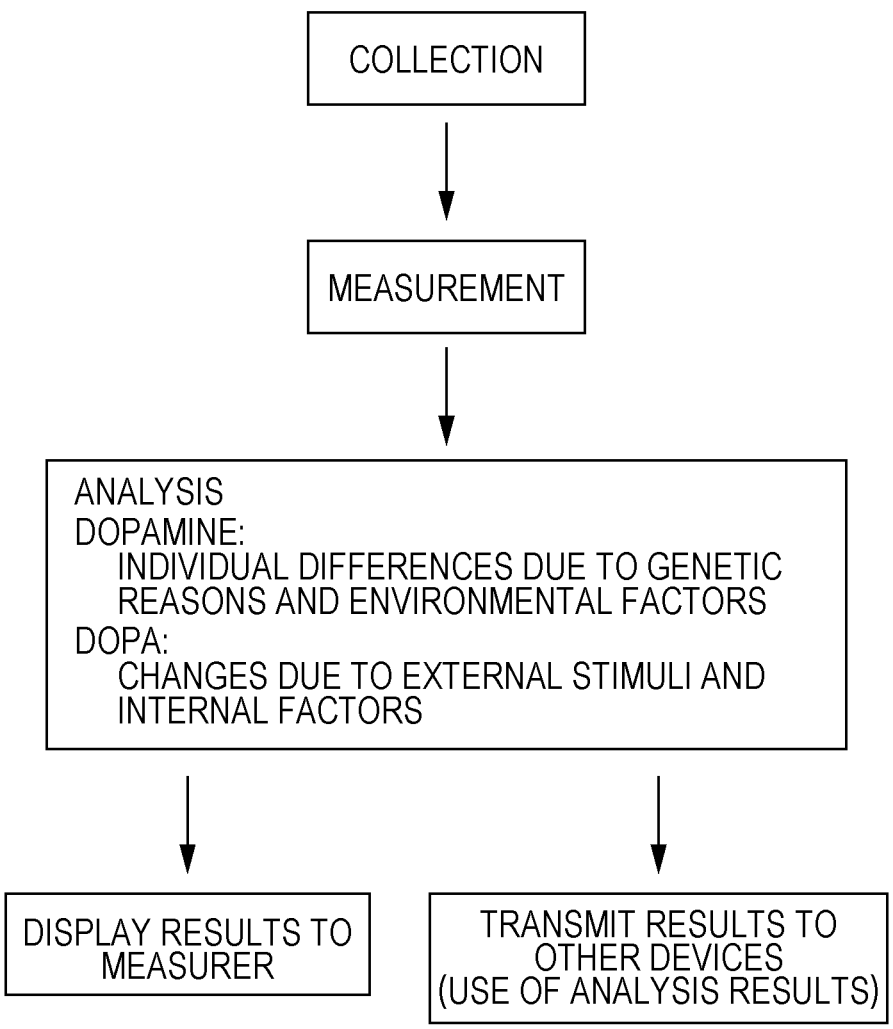
FIG. 23 is a diagram showing an overview of an embodiment of the present application.

Example 1 is implemented by the system configuration or procedures shown in FIG. 23 (acquisition of molecules on the skin). First, there is the collection unit of catecholamines from the skin surface, or the collection procedure.

The collection is realized by placing a liquid or solid material having an affinity to catecholamines in contact with the skin.

Second, there is the measurement unit of catecholamines from the skin surface, or the measurement procedure.

As the measurement methods, there are biochemical techniques and immunoassays that perform quantitative determination using absorptivity, fluorescence and color development according to structural changes of a substrate using enzymes and antibodies. Further, there is a method of performing quantitative determination of the enzymes and antibodies in combination with another sensor; for example, combination with a surface plasmon resonance (SPR) sensor, a semiconductor (FET) sensor, or an electrochemical sensor. Further, a method of performing quantitative determination from the electrification characteristics and mass spectrometry of the catecholamines, a method of combining chromatography and electrophoresis and the like may be exemplified.

Third, there is the measurement results analysis unit, or the analysis procedure.

Here, changes relating to the dopa amount according to the passing of time are extracted, and individual background amounts relating to the dopamine amount which do not depend upon the passing of time are extracted.

Fourth, there is the analysis result display unit or the display procedure, alternatively, there is the output unit transmitting the analysis result to another device or the transmission procedure.

Measurement was performed in practice with reference to the above procedures of FIG. 23 (acquisition of molecules on the skin).

To eight subjects, four loads of sleep, stress, recreation, and exercise were applied, and catecholamines were collected from the skin surface before and after each load. Further, in order to clarify the relationship with the physiological effects of catecholamine, measurement of blood pressure and pulse rate was performed as physiological indices at the same time as the skin catecholamine collection.

Regarding sleep, the subjects were asked to sleep in a bed from 13:00 to 14:30 after ingesting the same meal.

As the stress load, the Kraepelin test was performed for a total of 30 minutes with a five minute break therein. The Kraepelin test is a test in which adjacent digits are added together in one line of a column of digits and the digit from the units column of the answer is filled in.

For recreation, after viewing 3D video content for 30 minutes, the subjects were asked to play a 3D video game.

As the exercise load, an ergometer (FUKUDA DENSHI BE-360 Well Bike) was used, for the first 4 minutes, the load was 40 W, and for each minute thereafter, the load was increased by 40 W until the subjects reached a pedaling limit of a speed of 50 rotations per minute.

Catecholamine collection from the skin surface was performed using a dedicated collection tube; 60 μL of ultrapure water was placed in contact with the tips of the middle fingers of both hands for 3 minutes and the ultrapure water was recovered.

In the analysis of the catecholamines, a high performance liquid chromatography (HPLC) electrochemical detector (ECD) (SHISEIDO, NANOSPACE SI-2) was used. As the separation column, CAPCELL PAK C18 type: UG120 3 μm size: 1.5 mm i.d.×250 mm was used, as the mobile phase, 1.0 mM sodium octane-1-sulfonate, 0.02 mM EDTA-2Na, 10 mM $KH_2PO_4$, 0.05 vol % $H_3PO_4$ was used, and analysis was performed at a 180 μL/min flow rate, 30° C. column temperature, and ECD applied voltage of 800 mV (for example, refer to FIG. 4).

To quantify the individual catecholamines, a concentration reference solution of L-dopa (DOPA), dopamine (DA), norepinephrine (NE), and epinephrine (E) was analyzed, respective calibration curves were created, and the concentration was calculated from each calibration curve. Collection samples from the middle fingers of both hands were analyzed separately, and the average value was obtained.

The blood pressure and pulse rate measurements were average values measured three times each.

To evaluate the changes of each measurement value before and after the four loads of sleep, stress, recreation, and exercise, the changes were compared using the ratio of after the load/before the load and, as a result, it was seen that there was a tendency for DOPA to be reduced by sleep, and to be increased by the loads of stress and exercise (FIG. 20). According to Tukey multiple analysis, compared to sleep and recreation, the ratio of before and after the exercise load was a significantly higher value. No significant changes were seen in the DA. When the relationship between blood pressure and heart rate, which are physiological indices of catecholamines, relating to the DOPA seen in significant changes was analyzed, changes in the DOPA before and after the loads and a significant correlation in the changes in systolic blood pressure and heart rate before and after the load was seen (FIG. 21). The amount of skin DOPA is thought to be suitable for evaluating changes due to various factors.

When the individual differences between the averages of the individual catecholamines are evaluated, the collection amounts of NE and E were small compared to DOPA and DA, and, in comparison with the DOPA and DA having comparatively large collection amounts, the individual differences of the DA were great (FIG. 19). Compared to the CV value, the DA was 0.677 with respect to DOPA of 0.386, whereby the DOPA amount suitable for evaluating changes due to the loads had comparatively small individual differences and the individual differences of the DA were large. When the relationship of the respective individual averages of the DA amounts with large individual differences and the respective individual averages of the physiological indices was analyzed, there was a significant correlation with systolic blood pressure (maximum blood pressure) (FIG. 22). The amount of skin DA is thought to be more suitable for evaluating background amounts due to individual differences rather than changes due to various factors.

Example 2

Monoamines

In order to analyze external stimuli and internal factors from changes in the DOPA amount on the skin as well as individual differences from the amount of DA on the skin, it is preferable that a plurality of samples be taken over time and measured. In this case, as shown in the example, the change amount of the DOPA over time and the DA amount according to the average values are analyzed.

To perform analysis from a single or several collections and measurements, the amount of DOPA and the amount of DA are estimated from the comparative ratios of each catecholamine, and the respective increases or decreases and sizes thereof are predicted.

Example 3

Monoamines

Figure 24:
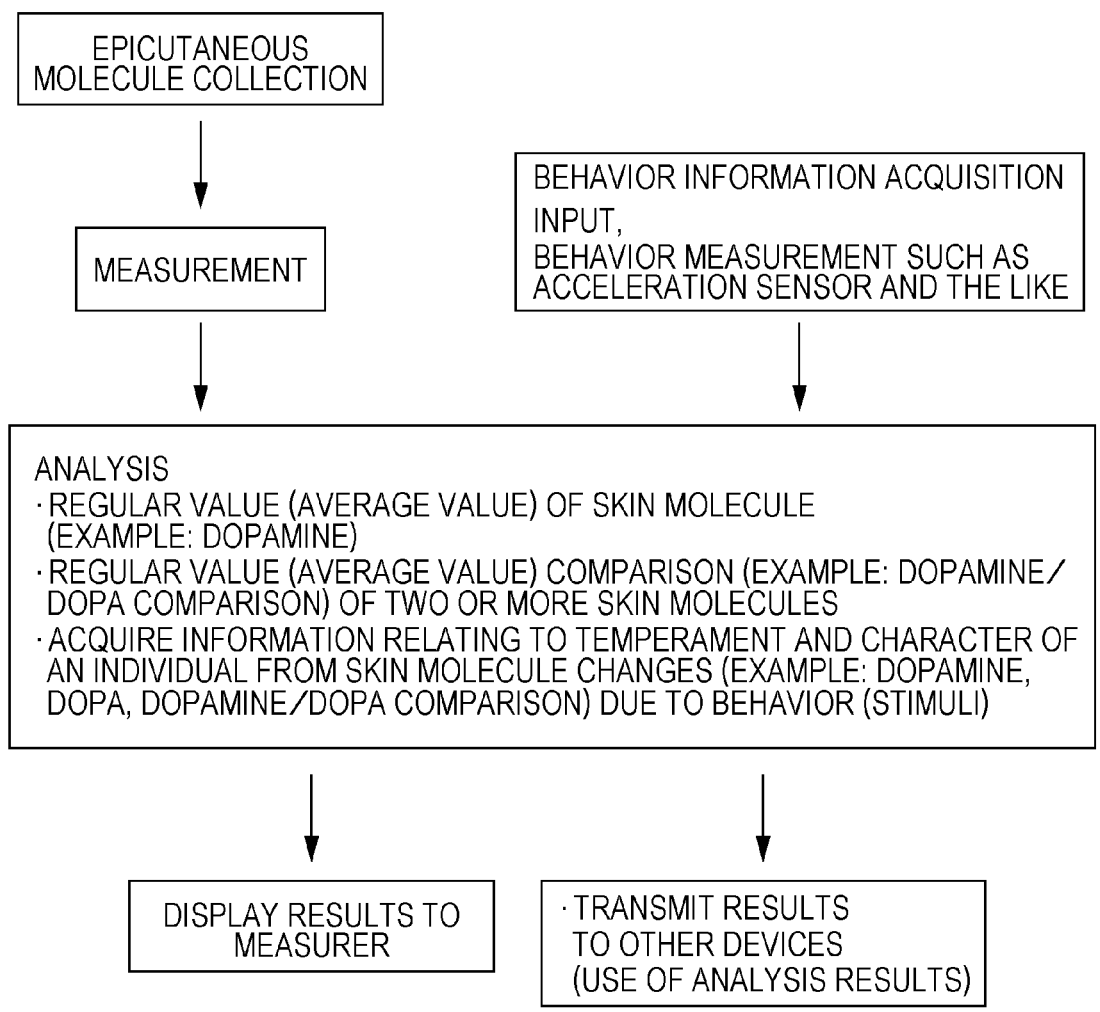
FIG. 24 is a diagram showing an overview of the embodiment of the present application.

Example 3 is implemented by the system configuration or procedures shown in FIG. 24 (acquisition of molecules on the skin and acquisition of activity information).

First, there is the collection unit of biomolecules from the skin surface, or the collection procedure.

The collection is performed by placing a liquid or solid material having an affinity with the biomolecules that are the measurement target in contact with the skin.

Second, there is the biomolecule measurement unit, or the measurement procedure.

As the measurement methods, there are biochemical techniques and immunoassays that perform quantitative determination using absorptivity, fluorescence and color development according to structural changes of a substrate using enzymes and antibodies. Further, there is a method of performing quantitative determination of the enzymes and antibodies in combination with another sensor; for example, combination with a surface plasmon resonance (SPR) sensor, a semiconductor (FET) sensor, or an electrochemical sensor. Further, a method of performing quantitative determination from the electrification characteristics and mass spectrometry of the target biomolecules, a method of combining chromatography and electrophoresis and the like may be exemplified.

Third, there is the site for acquiring the activity information, or the procedure therefor.

The acquisition of the activity information may be performed by a method in which the measurer himself or herself performs the inputting, or using an action plan using an accelerometer or the like.

Fourth, there is the analysis unit, or the analysis procedure.

In the analysis, a table or a conversion formula for converting the biomolecules measured on the skin or the amount or quantity ratio of the molecule groups into the temperament and character information are prepared.

Then, by applying the table or conversion formula to the measurement results of the molecules on the skin, temperament and character information is created.

The information of the molecules on the skin which may be converted into character information may be exemplified in the following manner.

Normal values of specific molecules on the skin, that is, measurement values according to a set schedule, average daily values or the like. For example, the amount of dopamine upon awakening and the average daily value.

Normal values of the quantity ratio of two or more molecules on the skin. For example, the value of the dopamine/dopa ratio upon awakening and the daily average.

Changes in molecules on the skin due to activities and stimuli. For example, changes in dopamine and the dopamine/dopa ratio before and after sleep and exercise.

Fifth, there is the analysis result display unit or the display procedure, alternatively, there is the output unit transmitting the analysis result to another device or the transmission procedure.

Measurement was performed in practice with reference to the above procedures of FIG. 24 (acquisition of molecules on the skin and acquisition of activity information).

To eight subjects, four loads of sleep, stress, recreation, and exercise were applied, and monoamines (dopamine, adrenaline, noradrenaline, and dopa) were collected from the skin surface before and after each load.

The determination of the temperament and character of the subject was implemented by performing a TCI test. The TCI test is a questionnaire test relating to the four measures of temperament and three of character shown in FIG. 6, which are respectively represented as points from 0 to 100.

Regarding sleep, the subjects were asked to sleep in a bed from 13:00 to 14:30 after ingesting the same meal.

As the stress load, the Kraepelin test was performed for a total of 30 minutes with a five minute break therein. The Kraepelin test is a test in which adjacent digits are added together in one line of a column of digits and the digit from the units column of the answer is filled in.

For recreation, after viewing 3D video content for 30 minutes, the subjects were asked to play a 3D video game.

As the exercise load, an ergometer (FUKUDA DENSHI BE-360 Well Bike) was used, for the first 4 minutes, the load was 40 W, and for each minute thereafter, the load was increased by 40 W until the subjects reached a pedaling limit of a speed of 50 rotations per minute.

Catecholamine collection from the skin surface was performed using a dedicated collection tube; 60 μL of ultrapure water was placed in contact with the tips of the middle fingers of both hands for 3 minutes and the ultrapure water was recovered.

In the analysis of the catecholamines, a high performance liquid chromatography (HPLC) electrochemical detector (ECD) (SHISEIDO, NANOSPACE SI-2) was used. As the separation column, CAPCELL PAK C18 type: UG120 3 μm size: 1.5 mm i.d.×250 mm was used, as the mobile phase, 1.0 mM sodium octane-1-sulfonate, 0.02 mM EDTA-2Na, 10 mM $KH_2PO_4$, 0.05 vol % $H_3PO_4$ was used, and analysis was performed at a 180 μL/min flow rate, 30° C. column temperature, and ECD applied voltage of 800 mV. To quantify the individual catecholamines, a concentration reference solution of L-dopa (DOPA), dopamine (DA), norepinephrine (NE), and epinephrine (E) was analyzed, respective calibration curves were created, and the concentration was calculated from each calibration curve. Collection samples from the middle fingers of both hands were analyzed separately, and the average value was obtained.

The results are shown below.

Figure 7:
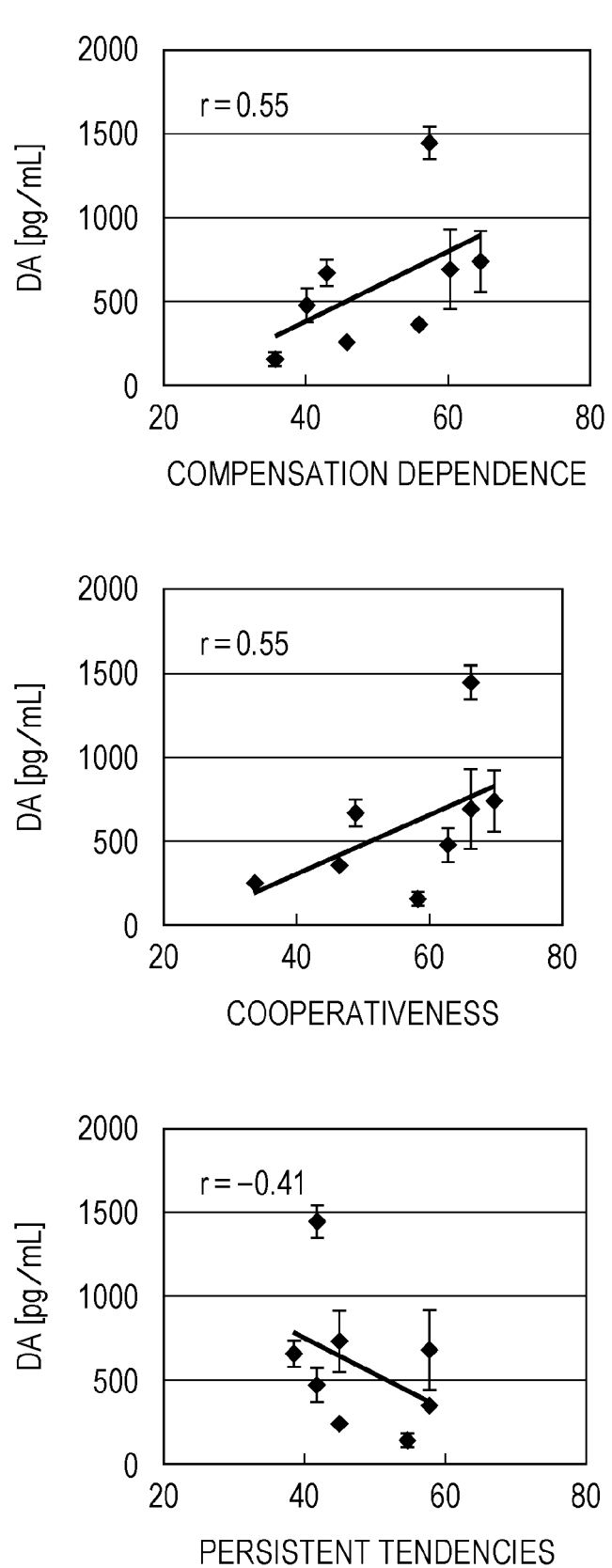
FIG. 7 is a diagram showing a correlation between character and dopamine average values in an embodiment of the present application.

There is a correlation between the normal values of dopamine (average values for one day) and temperament traits of compensation dependence and persistent tendencies and character traits of cooperativeness (refer to FIG. 7).

There is a correlation between the normal values of the dopamine/dopa ratio (average values for one day) and temperament traits of persistent tendencies (refer to FIG. 8).

The normal values of dopamine (average values for one day) have a negative correlation with the before and after sleep ratio of dopamine and dopa, and a positive correlation with the before and after exercise ratio (refer to FIG. 9). That is, for people for whom the normal values of dopamine are great, dopamine and dopa are likely to deteriorate during rest such as sleep and likely to increase during exercise. There is no correlation with character; however, it is shown that individuality is represented.

There is a negative correlation between the before and after sleep ratio of dopamine and the before and after stress, recreation, and exercise ratios of dopamine; there is a positive correlation between the before and after stress ratio of dopamine and the before and after recreation and exercise ratios respectively; and there is a positive correlation between the before and after recreation ratio of dopamine and the before and after exercise ratio (refer to FIG. 10). The more a person is likely to undergo deterioration of dopamine due to rest such as sleep, the more likely it is that the dopamine will be increased by active behavior such as stress, recreation, and exercise. This does not have a correlation with character either; however, it is shown that individuality is represented.

There are correlation patterns between each of temperament and character and the change ratios of each before and after activity ratio of dopamine, dopa, and the dopamine/dopa ratio.

FIG. 5 schematically shows a correlation between each of temperament and character and the change ratios of each before and after activity ratio of dopamine, dopa, and the dopamine/dopa ratio.

An upward arrow shows a positive correlation with the change ratio, a downward arrow shows a negative correlation, and a dash shows that there is no correlation. In each of temperament and character, there are correlations with specific activities, and it is possible to isolate different temperament and character traits from the differences in the patterns and define the character. FIGS. 11 to 18 show the results of correlations between different temperament and character traits and the change ratios of dopamine, dopa, and the dopamine/dopa ratio due to activities.

As described above, since there is a correlation between the temperament and character assessment of the TCI test and the dopamine normal values, the dopamine/dopa ratio normal values, and the changes in dopamine, dopa and the dopamine/dopa ratio before and after each activity, it is shown that it is possible to define temperament and character from molecules on the skin.

Example 4

Monoamines

If the molecules which are the target of measurement are molecules which may be measured on the skin and molecules adopted by the central nervous system and peripheral nerves, all may be targeted.

Specific character traits (desire or sexual preference) may be taken from those character traits classified by temperament, character, and the TCI test. Tables and conversion formulas for conversion to character trait to be defined may be prepared. There are cases where a combined system in which components which do not change according to growth and maturity such as temperament are determined by a questionnaire or the like and character components which do change according to growth and maturity are determined from molecules on the skin is effective.

The activity information may not only be input by the input of the measurer or a plan of action, but also obtained by analyzing changes of molecule groups.

Information regarding skin structure and blood vessels that may be collected from the skin, information regarding peripheral nerves and autonomic nerves, heart rate and blood pressure, body temperature, sweat rate, and the like is electrically and optically obtained. This information is combined with information relating to the molecules, whereby it is possible to obtain more detailed information.

Example 5

Steroid Hormones

Here, the Iowa gambling task is a test widely used in cognitive and emotional research to mimic real world decision-making. The experiment participants (subjects) are presented with four virtual card decks on a computer screen. Each chooses a card each time and gains or loses the amount of game money written on the back of the card. The purpose of this test (goal) is to gain as much money as possible. The experiment participants are asked to choose cards according to "intuition" rather than by consciously thinking. Two of the decks are "bad decks" for which the long-term balance will be negative. The other two decks are "good decks" for which the long-term balance will be positive.

Here, most of the experiment participants (healthy persons) will stick to the good decks after about 40 to 50 selections. People with a high risk-taking tendency have a high rate of selecting the "bad decks" and people with a low risk-taking tendency have a high rate of selecting the "good decks". The number of times that a person chose the bad deck after choosing 100 cards is set as the risk-taking rate for that person.

Sample collection and saliva collection was performed by the method of placing the fingertips in contact with water, and the testosterone and cortisol of the subjects was measured. The measurement method is an inhibition method using ELISA and an SPR sensor.

On the other hand, as a method to determine the risk-taking tendency of each subject, the above-described Iowa gambling task was used.

A correlation was found between these and the risk-taking rate obtained in the Iowa gambling task, and the results are shown in Table 2 (15 subjects in the experiment) and FIG. 26 (33 subjects in the experiment).

Table 2 showed that the testosterone collected from the finger had the highest correlation with the risk-taking rate. From the results in Table 2, the variation in the testosterone and cortisol in the saliva was large.

As the results of FIGS. 1A and B, the correlation coefficient of the risk-taking rate and testosterone of the skin was 0.46 (p=0.0067).

TABLE 2

Correlation Relationship Between
Testosterone And Cortisol Concentration
And Risk-Taking Ratio

|  | r | p |
|---|---|---|
| Testosterone (skin) | 0.55 | 0.032 |
| Testosterone (saliva) | 0.26 | 0.351 |
| Cortisol (skin) | 0.44 | 0.105 |
| Cortisol (saliva) | −0.05 | NA |

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An individual information determining method comprising:
    collecting one or a plurality of biomolecules from a body surface of a subject using a measurement apparatus;
    calculating a quantity of the one or the plurality of biomolecules collected;
    transmitting information about the quantity of the one or the plurality of biomolecules collected by the measurement apparatus to a body surface biomolecule data processing unit;
    transmitting the information from the biomolecule data processing unit to an individual information analysis unit, wherein the information is body surface biomolecule data that specifies at least the quantity of the one or the plurality of biomolecules collected from the body surface of the subject;
    selecting conversion information stored within the individual information analysis unit, wherein the conversion information converts the body surface biomolecule data into individual information about the subject;
    applying the conversion information to the body surface biomolecule data and selecting individual information that correlates to the body surface biomolecule data;
    and further comprising:
    collecting living activity data from the subject in a living acquisition unit;
    transmitting the living activity data from the living acquisition unit to a living activity data processing unit;
    transmitting the living activity data from the living activity data processing unit to the individual information analysis unit;
    combining the body surface biomolecule data and the living activity data in the individual information analysis unit; and
    selecting one or both of the body surface biomolecule data and the living activity data in the conversion information to determine the individual information about the subject.

2. The individual information determining method according to claim 1, wherein the living activity data are living activity classification data.

3. The individual information determining method according to claim 1, wherein the one or the plurality of biomolecules from the body surface of the subject are monoamines or steroid hormones.

4. The individual information determining method according to claim 3, wherein the monoamines are one or both of dopamine and L-dopa biomolecule data.

5. The individual information determining method according to claim 4, wherein one or both of dopamine and L-dopa is collected as the one or the plurality of biomolecules from the body surface of the subject,
    wherein the individual information that is determined based on the selected conversion information is temperament traits and character traits, and wherein
    the temperament traits comprise: pursuit of novelty, damage avoidance, compensation dependence, and persistent tendencies and the character traits comprise: self-orientation, cooperativeness, and self-transcendence.

6. The individual information determining method according to claim 5, wherein dopamine is collected as the one or the plurality of biomolecules from the body surface of the subject and an average value of the dopamine collected is calculated, and wherein the temperament traits of persistent tendencies as well as the character traits of compensation dependence and cooperativeness are determined based on the average value of the dopamine.

7. The individual information determining method according to claim 5, wherein dopamine and L-dopa are collected as the one or the plurality of biomolecules from the body surface of the subject and a ratio of dopamine to L-dopa is calculated, wherein an average value of the ratio is calculated, and wherein the temperament traits of pursuit of novelty and persistent tendencies are determined based on the average value of the ratio.

8. The individual information determining method according to claim 5, wherein
    (a) temperament traits of persistent tendencies and character traits of self-orientation based on sleep data,
    (b) temperament traits of compensation dependence as well as character traits of self-orientation, and self-transcendence based on stress data,
    (c) temperament traits of persistent tendencies as well as character traits of self-orientation, cooperativeness, and self-transcendence based on recreation data, and
    (d) temperament traits of damage avoidance and persistent tendencies as well as character traits of self-orientation, cooperativeness, and self-transcendence based on exercise data, are determined from the dopamine collected as the one or the plurality of biomolecules from the body surface of the subject and the living activity data.

9. The individual information determining method according to claim 5, wherein
    (a) temperament traits of compensation dependence as well as character traits of cooperativeness based on sleep data,
    (b) temperament traits of damage avoidance as well as character traits of self-orientation and cooperativeness based on stress data,
    (c) temperament traits of pursuit of novelty and persistent tendencies as well as character traits of self-orientation and cooperativeness based on recreation data, and
    (d) temperament traits of pursuit of novelty, compensation dependence and persistent tendencies as well as character traits of cooperativeness and self-transcendence based on exercise data, are determined from the L-dopa collected as the one or the plurality of biomolecules from the body surface of the subject and the living activity data.

10. The individual information determining method according to claim 5, wherein (a) temperament traits of persistent tendencies as well as character traits of self-orientation based on sleep data,
(b) temperament traits of damage avoidance as well as character traits of self-orientation, cooperativeness, and self-transcendence based on stress data,
(c) character traits of self-orientation, cooperativeness, and self-transcendence based on recreation data, and
(d) temperament traits of pursuit of novelty, damage avoidance, and persistent tendencies based on exercise data, are determined from a ratio of dopamine collected as the one or the plurality of biomolecules from the body surface of the subject to L-dopa collected as the one or the plurality of biomolecules from the body surface of the subject and the living activity data.

11. The individual information determining method according to claim 1, wherein the one or the plurality of biomolecules from the body surface is testosterone, and wherein a tendency to be aggressive and dominant in living activities, a tendency to take risks, a compensation dependence tendency, and a tendency not to trust others are determined from the testosterone quantity.

12. The individual information determining method according to claim 1, wherein the collecting one or a plurality of biomolecules from the body surface of the subject comprises applying a solvent having an affinity for the biomolecules to the body surface and taking the biomolecules into the solvent.

13. The individual information determining method according to claim 1, wherein the living activity data comprises: sleep, stress, recreation, and exercise.

\* \* \* \* \*